US008722050B2

(12) United States Patent
Qiu

(10) Patent No.: US 8,722,050 B2
(45) Date of Patent: May 13, 2014

(54) METHOD OF TREATING VIRUS-INDUCED CANCER

(71) Applicant: Pheromonicin Biotech, Ltd., Tortola (VG)

(72) Inventor: Xiao-Qing Qiu, Beijing (CN)

(73) Assignee: Pheromonicin Biotech, Ltd., Road Town (VG)

( * ) Notice: Subject to any disclaimer, the term of this patent is extended or adjusted under 35 U.S.C. 154(b) by 0 days.

(21) Appl. No.: 13/708,767

(22) Filed: Dec. 7, 2012

(65) Prior Publication Data

US 2013/0142797 A1 Jun. 6, 2013

Related U.S. Application Data

(62) Division of application No. 11/297,464, filed on Dec. 9, 2005, now Pat. No. 8,367,066.

(30) Foreign Application Priority Data

Dec. 10, 2004 (CN) .......................... 2004 1 0081446

(51) Int. Cl.
*A61K 39/395* (2006.01)

(52) U.S. Cl.
USPC ...................................................... 424/183.1

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. |
| 4,873,191 A | 10/1989 | Wagner et al. |
| 4,873,316 A | 10/1989 | Meade et al. |
| 2006/0233813 A1 | 10/2006 | Qiu |

FOREIGN PATENT DOCUMENTS

| | | |
|---|---|---|
| EP | 0 264 166 A1 | 4/1988 |
| WO | 96/09398 A1 | 3/1996 |
| WO | 97/07668 A1 | 3/1997 |
| WO | 97/07669 A1 | 3/1997 |

OTHER PUBLICATIONS

Fitzgerald et al. (Int. J. Med. Microbiol., 293:577-582, Apr. 2004).*
Lasko, et al., "Targeted Oncogene Activation by Site-Specific Recombination in Transgenic Mice," Proc. Natl. Acad. Sci. USA, vol. 89, pp. 6232-6236, Jul. 1992.
O'Gorman, et al., "Recombinase-Mediated Gene Activation and Site-Specific Integration in Mammalian Cells," Science, vol. 251, No. 4999, pp. 1351-1355, Mar. 15, 1991.
Wilmut, et al Offspring Derived from Fetal and Adult Mammalian Cells, Nature, vol. 385, pp. 810-813, Feb. 27, 1997.
Hogan, et al the Mouse Embryo: A Laboratory Manual: Section D—Introduction of New Genetic Information, Cold Spring Harbor Laboratory Press, Cold Spring Harbor, NY, 1986.
Pinkert, et al., "An Albumin Enhancer Located 10 kb Upstream Functions along with its Promoter to Direct Efficient, Liver-Specific Expression in Transgenic Mice," Genes & Development, vol. 1, pp. 268-276, 1987.
Winoto, et al., "A Novel, Inducible and T-Cell-Specific Enhancer Located at the 3 End of the T-Cell Receptor Alpha Locus," The EMBO Journal, vol. 8, No. 3, pp. 729-733, 1989.
Banerji, et al., "A Lymphocyte-Specific Cellular Enhancer is Located Downstream of the Joining Region in Immunoglobulin Heavy Chain Genes," Cell, vol. 33, pp. 729-740, Jul. 1983.
Byrne, et al Gene Regulation: A Two-Tiered Approach to Transgene Regulation in Transgenic Mice, Proc. Natl. Acad. Sci. USA, vol. 86, pp. 5473-5477, Jul. 1989.
Wada, et al., "Codon Usage Tabulated from the Genbank Genetic Sequence Data," Nucleic Acids Research, vol. 20, Supplement, pp. 2111-2118, 1992.
Baldari, et al., "A Novel Leader Peptide which allows Efficient Secretion of a Fragment of Human interleukin 1 [3 in *Saccharomyces cerevisiae*," The EMBO Journal, vol. 6, No. 1, pp. 229-234, 1987.
Smith, et al., "Production of Human Beta Interferon in Insect Cells Infected with a Baculovirus Expression Vector," Molecular and Cellular Biology, vol. 3, No. 12, pp. 2156-2165, Dec. 1983.
Kaufman, et al Efficiency of Polycistronic mRNAs and their Utilization to Express Heterologous Genes in Mammalian Cells, The EMBO Journal, vol. 6, No. 1, pp. 187-193, 1987.
Camper, et al., "Postnatal Repression of the Alpha-Fetoprotein Gene is Enhancer Independent," Genes & Development, vol. 3, pp. 537-546, 1989.
Goeddel, Gene Expression Technology: Methods in Enzymology, 185, Academic Press, San Diego, CA, 1990 (cited on page 14, paragraphs [0068] and [0069]).
Amann, et al regulated tac promoter vectors useful for the expression of unfused and fused proteins in *Escherichia coli*, Gene, vol. 69, Issue 2, pp. 301-315 (cited on page 17, paragraph [0071] 1988.
Sambrook, et al., "Molecular Cloning: A Laboratory Manual—Chapters 16 and 17", Second Edition, Cold Springs Harbor Laboratory, Cold Spring Harbor Laboratory Press, 1989 (cited on page 16, paragraph [0075] and page 17, paragraph [0078]).
Studier et al., Gene Expression Technology: Method in Enzymology 185. Academic Press. San Diego, CA, pp. 69-89, Jun. 11, 1990.
Gottesman, Susan, Gene Expression Technology: Method in Enzymology 185. Academic Press, San Diego. CA, pp. 119-128, Jun. 11, 1990.
Smith et al., "Single-step purification of polypeptides expressed in *Escherichia coil* as fusions with glutathione S-transferase," Gene, vol. 67. Issue 1. pp. 31-40, Jul. 15, 1988.
Amann et al., Tightly regulated tac promoter vectors useful for the expression of unfused and fused proteins in *Escherichia coil*, Gene, vol. 69, Issue 2. pp. 301-315, Sep. 30, 1988.

(Continued)

*Primary Examiner* — Brian J Gangle
(74) *Attorney, Agent, or Firm* — Maschoff Brennan

(57) ABSTRACT

The present invention relates to methods of treating virus-induced cancer with the polypeptides that are capable of killing cells. The polypeptide comprises a targeting agent covalently attached to a channel-forming moiety. In a preferred embodiment, the channel-forming moiety comprises a colicin and the targeting agent is a reconstructed antibody mimetic derived from monoclonal antibody variants against Epstein-Barr virus gp350/220.

19 Claims, 10 Drawing Sheets

(56) References Cited

OTHER PUBLICATIONS

Kurjan et al., Structure of a yeast pheromone gene (ME alpha): a putative alpha-factor precursor contains four tandem copies of mature alpha-factor, Cell, vol. 30. pp. 933-943, 1982.
Schultz et al., "Expression and secretion in yeast of a 400-kda envelope alycoprotein derived from epstein-barr virus," Gene, vol. 54, Issue 1, pp. 113-123, 1987.
Lucklow et al., "High level expression of nonfused foreign genes with *Autographa califomia* nuclear polvhedrosis virus expression vectors," Virology, vol. 170, Issue 1. pp. 31-39, May 1989.
Seed, Brian, "An LEA-3 cDNA_encodes a phospholipid-linked membrane protein homologous to its receptor CD2," Nature, vol. 329, p. 840-842, Oct. 29, 1987.
Calame et al., "Transcriptional Controlling Elements in the Immunoglobulin and T Cell Receptor Loci," Adv. Immunol., vol. 43, pp. 235-275, 1988.
Queen et al., "Immunoglobulin gene transcription is activated by downstream sequence elements," Cell, vol. 33, pp. 741-748, 1983.
Kessel et al., "Murine development control genes," Science, vol. 249, pp. 374-379, 1990.
Rabanus et al. (Amer. J. Pathol., 139:185-197, 1991).
Cruse et al. (Illustrated Dictionary of Immunol., CRC Press, 2003, p. 333).
Hoffman et al. (PNAS, 77:2979-2983, 1980).
Thorley-Lawson et al. (PNAS, 77:5307-5311, 1980).
Qiu et al. (Nature Biotechnol., 21:1480-1485, 2003).
Stroud et al. (Curr. Opinion Struc. Biol., 8:525-533, 1998).

* cited by examiner

```
                              SEQUENCE LISTING

<160> NUMBER OF SEQ ID NOS: 12

<210> SEQ ID NO 1
<211> LENGTH: 626
<212> TYPE: PRT
<213> ORGANISM: Escherichia coli

<400> SEQUENCE: 1

Met Ser Asp Pro Val Arg Ile Thr Asn Pro Gly Ala Glu Ser Leu Gly
1               5                   10                  15

Tyr Asp Ser Asp Gly His Glu Ile Met Ala Val Asp Ile Tyr Val Asn
            20                  25                  30

Pro Pro Arg Val Asp Val Phe His Gly Thr Pro Pro Ala Trp Ser Ser
        35                  40                  45

Phe Gly Asn Lys Thr Ile Trp Gly Gly Asn Glu Trp Val Asp Asp Ser
    50                  55                  60

Pro Thr Arg Ser Asp Ile Glu Lys Arg Asp Lys Glu Ile Thr Ala Tyr
65                  70                  75                  80

Lys Asn Thr Leu Ser Ala Gln Gln Lys Glu Asn Glu Asn Lys Arg Thr
                85                  90                  95

Glu Ala Gly Lys Arg Leu Ser Ala Ala Ile Ala Ala Arg Glu Lys Asp
            100                 105                 110

Glu Asn Thr Leu Lys Thr Leu Arg Ala Gly Asn Ala Asp Ala Ala Asp
        115                 120                 125

Ile Thr Arg Gln Glu Phe Arg Leu Leu Gln Ala Glu Leu Arg Glu Tyr
    130                 135                 140

Gly Phe Arg Thr Glu Ile Ala Gly Tyr Asp Ala Leu Arg Leu His Thr
145                 150                 155                 160

Glu Ser Arg Met Leu Phe Ala Asp Ala Asp Ser Leu Arg Ile Ser Pro
                165                 170                 175

Arg Glu Ala Arg Ser Leu Ile Glu Gln Ala Glu Lys Arg Gln Lys Asp
            180                 185                 190

Ala Gln Asn Ala Asp Lys Lys Ala Ala Asp Met Leu Ala Glu Tyr Glu
        195                 200                 205
```

-continued

```
Arg Arg Lys Gly Ile Leu Asp Thr Arg Leu Ser Glu Leu Glu Lys Asn
    210                 215                 220

Gly Gly Ala Ala Leu Ala Val Leu Asp Ala Gln Gln Ala Arg Leu Leu
225                 230                 235                 240

Gly Gln Gln Thr Arg Asn Asp Arg Ala Ile Ser Glu Ala Arg Asn Lys
                245                 250                 255

Leu Ser Ser Val Thr Glu Ser Leu Asn Thr Ala Arg Asn Ala Leu Thr
            260                 265                 270

Arg Ala Glu Gln Gln Leu Thr Gln Gln Lys Asn Thr Pro Asp Gly Lys
        275                 280                 285

Thr Ile Val Ser Pro Glu Lys Phe Pro Gly Arg Ser Ser Thr Asn His
    290                 295                 300

Ser Ile Val Val Ser Gly Asp Pro Arg Phe Ala Gly Thr Ile Lys Ile
305                 310                 315                 320

Thr Thr Ser Ala Val Ile Asp Asn Arg Ala Asn Leu Asn Tyr Leu Leu
                325                 330                 335

Ser His Ser Gly Leu Asp Tyr Lys Arg Asn Ile Leu Asn Asp Arg Asn
            340                 345                 350

Pro Val Val Thr Glu Asp Val Glu Gly Asp Lys Lys Ile Tyr Asn Ala
        355                 360                 365

Glu Val Ala Glu Trp Asp Lys Leu Arg Gln Arg Leu Leu Asp Ala Arg
    370                 375                 380

Asn Lys Ile Thr Ser Ala Glu Ser Ala Val Asn Ser Ala Arg Asn Asn
385                 390                 395                 400

Leu Ser Ala Arg Thr Asn Glu Gln Lys His Ala Asn Asp Ala Leu Asn
                405                 410                 415

Ala Leu Leu Lys Glu Lys Glu Asn Ile Arg Asn Gln Leu Ser Gly Ile
            420                 425                 430

Asn Gln Lys Ile Ala Glu Glu Lys Arg Lys Gln Asp Glu Leu Lys Ala
        435                 440                 445

Thr Lys Asp Ala Ile Asn Phe Thr Thr Glu Phe Leu Lys Ser Val Ser
    450                 455                 460

Glu Lys Tyr Gly Ala Lys Ala Glu Gln Leu Ala Arg Glu Met Ala Gly
465                 470                 475                 480

Gln Ala Lys Gly Lys Lys Ile Arg Asn Val Glu Glu Ala Leu Lys Thr
                485                 490                 495

Tyr Glu Lys Tyr Arg Ala Asp Ile Asn Lys Lys Ile Asn Ala Lys Asp
            500                 505                 510

Arg Ala Ala Ile Ala Ala Ala Leu Glu Ser Val Lys Leu Ser Asp Ile
        515                 520                 525

Ser Ser Asn Leu Asn Arg Phe Ser Arg Gly Leu Gly Tyr Ala Gly Lys
    530                 535                 540

Phe Thr Ser Leu Ala Asp Trp Ile Thr Glu Phe Gly Lys Ala Val Arg
545                 550                 555                 560

Thr Glu Asn Trp Arg Pro Leu Phe Val Lys Thr Glu Thr Ile Ile Ala
                565                 570                 575

Gly Asn Ala Ala Thr Ala Leu Val Ala Leu Val Phe Ser Ile Leu Thr
            580                 585                 590

Gly Ser Ala Leu Gly Ile Ile Gly Tyr Gly Leu Leu Met Ala Val Thr
        595                 600                 605

Gly Ala Leu Ile Asp Glu Ser Leu Val Glu Lys Ala Asn Lys Phe Trp
    610                 615                 620

Gly Ile
```

625

<210> SEQ ID NO 2
<211> LENGTH: 1878
<212> TYPE: DNA
<213> ORGANISM: Escherichia coli

<400> SEQUENCE: 2

```
atgtctgacc ctgtacgtat tacaaatccc ggtgcagaat cgctggggta tgattcagat     60
ggccatgaaa ttatggccgt tgatatttat gtaaaccctc cacgtgtcga tgtctttcat    120
ggtaccccgc ctgcatggag ttccttcggg aacaaaacca tctggggcgg aaacgagtgg    180
gttgatgatt ccccaacccg aagtgatatc gaaaaaaggg acaaggaaat cacagcgtac    240
aaaaacacgc tcagcgcgca gcagaaagag aatgagaata agcgtactga agccggaaaa    300
cgcctctctg cggcgattgc tgcaagggaa aaagatgaaa acacactgaa aacactccgt    360
gccggaaacg cagatgccgc tgatattaca cgacaggagt tcagactcct gcaggcagag    420
ctgagagaat acggattccg tactgaaatc gccggatatg acgccctccg gctgcataca    480
gagagccgga tgctgtttgc tgatgctgat tctcttcgta tatctccccg ggaggccagg    540
tcgttaatcg aacaggctga aaaacggcag aaggatgcgc agaacgcaga caagaaggcc    600
gctgatatgc ttgctgaata cgagcgcaga aaaggtattc tggacacccg gttgtcagag    660
ctggaaaaaa atggcggggc agcccttgcc gttcttgatg cacaacaggc ccgtctgctc    720
gggcagcaga cacggaatga cagggccatt tcagaggccc ggaataaact cagttcagtg    780
acggaatcgc ttaacacggc ccgtaatgca ttaaccagag ctgaacaaca gctgacgcaa    840
cagaaaaaca cgcctgacgg caaaacgata gtttcccctg aaaaattccc ggggcgttca    900
tcaacaaatc attctattgt tgtgagcggt gatccgagat ttgccggtac gataaaaatc    960
acaaccagcg cagtcatcga taaccgtgca aacctgaatt atcttctgag ccattccggt   1020
ctggactata aacgcaatat tctgaatgac cggaatccgg tggtgacaga ggatgtggaa   1080
ggtgacaaga aaatttataa tgctgaagtt gctgaatggg ataagttacg gcaaagattg   1140
cttgatgcca gaaataaaat cacctctgct gaatctgcgg taaattcggc gagaaataac   1200
ctcagtgcca gaacaaatga gcaaaagcat gcaaatgacg ctcttaatgc cctgttgaag   1260
gaaaaagaga atatacgtaa ccagctttcc ggcatcaatc agaagatagc ggaagagaaa   1320
agaaaacagg atgaactgaa ggcaacgaaa gacgcaatta atttcacaac agagttcctg   1380
aaatcagttt cagaaaaata tggtgcaaaa gctgagcagt tagccagaga gatggccggg   1440
caggctaaag ggaagaaaat acgtaatgtt gaagaggcat taaaaacgta tgaaaagtac   1500
cgggctgaca ttaacaaaaa aattaatgca aaagatcgtg cagcgattgc cgcagccctt   1560
gagtctgtga agctgtctga tatatcgtct aatctgaaca gattcagtcg gggactggga   1620
tatgcaggaa aatttacaag tcttgctgac tggatcactg agtttggtaa ggctgtccgg   1680
acagagaact ggcgtcctct tttgttaaa acagaaacca tcatagcagg caatgccgca   1740
acggctcttg tggcactggt cttcagtatt cttaccggaa gcgctttagg cattatcggg   1800
tatggtttac tgatggctgt caccggtgcg ctgattgatg aatcgcttgt ggaaaaagcg   1860
aataagttct ggggtatt                                                   1878
```

<210> SEQ ID NO 3
<211> LENGTH: 176
<212> TYPE: PRT
<213> ORGANISM: Escherichia coli

<400> SEQUENCE: 3

```
Asp Ala Ile Asn Phe Thr Thr Glu Phe Leu Lys Ser Val Ser Glu Lys
1               5                   10                  15

Tyr Gly Ala Lys Ala Glu Gln Leu Ala Arg Glu Met Ala Gly Gln Ala
            20                  25                  30

Lys Gly Lys Lys Ile Arg Asn Val Glu Glu Ala Leu Lys Thr Tyr Glu
        35                  40                  45

Lys Tyr Arg Ala Asp Ile Asn Lys Lys Ile Asn Ala Lys Asp Arg Ala
    50                  55                  60

Ala Ile Ala Ala Ala Leu Glu Ser Val Lys Leu Ser Asp Ile Ser Ser
65                  70                  75                  80

Asn Leu Asn Arg Phe Ser Arg Gly Leu Gly Tyr Ala Gly Lys Phe Thr
                85                  90                  95

Ser Leu Ala Asp Trp Ile Thr Glu Phe Gly Lys Ala Val Arg Thr Glu
            100                 105                 110

Asn Trp Arg Pro Leu Phe Val Lys Thr Glu Thr Ile Ile Ala Gly Asn
        115                 120                 125

Ala Ala Thr Ala Leu Val Ala Leu Val Phe Ser Ile Leu Thr Gly Ser
    130                 135                 140

Ala Leu Gly Ile Ile Gly Tyr Gly Leu Leu Met Ala Val Thr Gly Ala
145                 150                 155                 160

Leu Ile Asp Glu Ser Leu Val Glu Lys Ala Asn Lys Phe Trp Gly Ile
                165                 170                 175
```

<210> SEQ ID NO 4
<211> LENGTH: 525
<212> TYPE: DNA
<213> ORGANISM: Escherichia coli

<400> SEQUENCE: 4

```
gcaattaatt tcacaacaga gttcctgaaa tcagtttcag aaaaatatgg tgcaaaagct      60

gagcagttag ccagagagat ggccgggcag gctaaaggga agaaaatacg taatgttgaa     120

gaggcattaa aaacgtatga aaagtaccgg gctgacatta acaaaaaaat taatgcaaaa     180

gatcgtgcag cgattgccgc agcccttgag tctgtgaagc tgtctgatat atcgtctaat     240

ctgaacagat tcagtcgggg actgggatat gcaggaaaat ttacaagtct tgctgactgg     300

atcactgagt ttggtaaggc tgtccggaca gagaactggc gtcctctttt tgttaaaaca     360

gaaaccatca tagcaggcaa tgccgcaacg gctcttgtgg cactggtctt cagtattctt     420

accggaagcg ctttaggcat tatcgggtat ggtttactga tggctgtcac cggtgcgctg     480

attgatgaat cgcttgtgga aaaagcgaat aagttctggg gtatt                     525
```

<210> SEQ ID NO 5
<211> LENGTH: 28
<212> TYPE: PRT
<213> ORGANISM: Artificial
<220> FEATURE:
<223> OTHER INFORMATION: Fusion peptide

<400> SEQUENCE: 5

```
Ser Phe Gly Met His Trp Val Arg Gln Ala Pro Glu Lys Gly Leu Glu
1               5                   10                  15

Trp Val Ala Gly Gln Gly Tyr Ser Tyr Pro Tyr Thr
            20                  25
```

<210> SEQ ID NO 6
<211> LENGTH: 84

-continued

<212> TYPE: DNA
<213> ORGANISM: Artificial
<220> FEATURE:
<223> OTHER INFORMATION: Nucleic acid sequence of a fusion peptide

<400> SEQUENCE: 6
tccttcggta tgcattgggt gcgtcaggcc cccgagaaag gtctggagtg ggtggccggt 60
cagggttact cctacccta cacc 84

<210> SEQ ID NO 7
<211> LENGTH: 654
<212> TYPE: PRT
<213> ORGANISM: Artificial
<220> FEATURE:
<223> OTHER INFORMATION: Fusion peptide

<400> SEQUENCE: 7

Met Ser Asp Pro Val Arg Ile Thr Asn Pro Gly Ala Glu Ser Leu Gly
1 5 10 15

Tyr Asp Ser Asp Gly His Glu Ile Met Ala Val Asp Ile Tyr Val Asn
20 25 30

Pro Pro Arg Val Asp Val Phe His Gly Thr Pro Pro Ala Trp Ser Ser
35 40 45

Phe Gly Asn Lys Thr Ile Trp Gly Gly Asn Glu Trp Val Asp Asp Ser
50 55 60

Pro Thr Arg Ser Asp Ile Glu Lys Arg Asp Lys Glu Ile Thr Ala Tyr
65 70 75 80

Lys Asn Thr Leu Ser Ala Gln Gln Lys Glu Asn Glu Asn Lys Arg Thr
85 90 95

Glu Ala Gly Lys Arg Leu Ser Ala Ala Ile Ala Ala Arg Glu Lys Asp
100 105 110

Glu Asn Thr Leu Lys Thr Leu Arg Ala Gly Asn Ala Asp Ala Ala Asp
115 120 125

Ile Thr Arg Gln Glu Phe Arg Leu Leu Gln Ala Glu Leu Arg Glu Tyr
130 135 140

Gly Phe Arg Thr Glu Ile Ala Gly Tyr Asp Ala Leu Arg Leu His Thr
145 150 155 160

Glu Ser Arg Met Leu Phe Ala Asp Ala Asp Ser Leu Arg Ile Ser Pro
165 170 175

Arg Glu Ala Arg Ser Leu Ile Glu Gln Ala Glu Lys Arg Gln Lys Asp
180 185 190

Ala Gln Asn Ala Asp Lys Lys Ala Ala Asp Met Leu Ala Glu Tyr Glu
195 200 205

Arg Arg Lys Gly Ile Leu Asp Thr Arg Leu Ser Glu Leu Glu Lys Asn
210 215 220

Gly Gly Ala Ala Leu Ala Val Leu Asp Ala Gln Gln Ala Arg Leu Leu
225 230 235 240

Gly Gln Gln Thr Arg Asn Asp Arg Ala Ile Ser Glu Ala Arg Asn Lys
245 250 255

Leu Ser Ser Val Thr Glu Ser Leu Asn Thr Ala Arg Asn Ala Leu Thr
260 265 270

Arg Ala Glu Gln Gln Leu Thr Gln Gln Lys Asn Thr Pro Asp Gly Lys
275 280 285

Thr Ile Val Ser Pro Glu Lys Phe Pro Gly Arg Ser Ser Thr Asn His
290 295 300

Ser Ile Val Val Ser Gly Asp Pro Arg Phe Ala Gly Thr Ile Lys Ile
305 310 315 320

```
Thr Thr Ser Ala Val Ile Asp Asn Arg Ala Asn Leu Asn Tyr Leu Leu
                325                 330                 335

Ser His Ser Gly Leu Asp Tyr Lys Arg Asn Ile Leu Asn Asp Arg Asn
            340                 345                 350

Pro Val Val Thr Glu Asp Val Glu Gly Asp Lys Lys Ile Tyr Asn Ala
        355                 360                 365

Glu Val Ala Glu Trp Asp Lys Leu Arg Gln Arg Leu Leu Asp Ala Arg
    370                 375                 380

Asn Lys Ile Thr Ser Ala Glu Ser Ala Val Asn Ser Ala Arg Asn Asn
385                 390                 395                 400

Leu Ser Ala Arg Thr Asn Glu Gln Lys His Ala Asn Asp Ala Leu Asn
                405                 410                 415

Ala Leu Leu Lys Glu Lys Glu Asn Ile Arg Asn Gln Leu Ser Gly Ile
            420                 425                 430

Asn Gln Lys Ile Ala Glu Glu Lys Arg Lys Gln Asp Glu Leu Lys Ala
        435                 440                 445

Thr Lys Asp Ala Ile Asn Phe Thr Thr Glu Phe Leu Lys Ser Val Ser
    450                 455                 460

Glu Lys Tyr Gly Ala Lys Ala Glu Gln Leu Ala Arg Glu Met Ala Gly
465                 470                 475                 480

Gln Ala Lys Gly Lys Lys Ile Arg Asn Val Glu Glu Ala Leu Lys Thr
                485                 490                 495

Tyr Glu Lys Tyr Arg Ala Asp Ile Asn Lys Lys Ile Asn Ala Lys Asp
            500                 505                 510

Arg Ala Ala Ile Ala Ala Ala Leu Glu Ser Val Lys Leu Ser Asp Ile
        515                 520                 525

Ser Ser Asn Leu Asn Arg Phe Ser Arg Gly Leu Gly Tyr Ala Gly Lys
    530                 535                 540

Phe Thr Ser Leu Ala Asp Trp Ile Thr Glu Phe Gly Lys Ala Val Arg
545                 550                 555                 560

Thr Glu Asn Trp Arg Pro Leu Phe Val Lys Thr Glu Thr Ile Ile Ala
                565                 570                 575

Gly Asn Ala Ala Thr Ala Leu Val Ala Leu Val Phe Ser Ile Leu Thr
            580                 585                 590

Gly Ser Ala Leu Gly Ile Ile Gly Tyr Gly Leu Leu Met Ala Val Thr
        595                 600                 605

Gly Ala Leu Ile Asp Glu Ser Leu Val Glu Lys Ala Asn Lys Phe Trp
    610                 615                 620

Gly Ile Ser Phe Gly Met His Trp Val Arg Gln Ala Pro Glu Lys Gly
625                 630                 635                 640

Leu Glu Trp Val Ala Gly Gln Gly Tyr Ser Tyr Pro Tyr Thr
                645                 650
```

<210> SEQ ID NO 8
<211> LENGTH: 1962
<212> TYPE: DNA
<213> ORGANISM: Artificial
<220> FEATURE:
<223> OTHER INFORMATION: Nucleic acid sequence of a fusion peptide

<400> SEQUENCE: 8

```
atgtctgacc ctgtacgtat tacaaatccc ggtgcagaat cgctggggta tgattcagat      60

ggccatgaaa ttatggccgt tgatatttat gtaaaccctc cacgtgtcga tgtctttcat     120

ggtaccccgc ctgcatggag ttccttcggg aacaaaacca tctggggcgg aaacgagtgg     180
```

-continued

```
gttgatgatt ccccaacccg aagtgatatc gaaaaaaggg acaaggaaat cacagcgtac    240

aaaaacacgc tcagcgcgca gcagaaagag aatgagaata agcgtactga agccggaaaa    300

cgcctctctg cggcgattgc tgcaagggaa aaagatgaaa acacactgaa aacactccgt    360

gccggaaacg cagatgccgc tgatattaca cgacaggagt tcagactcct gcaggcagag    420

ctgagagaat acggattccg tactgaaatc gccggatatg acgccctccg gctgcataca    480

gagagccgga tgctgtttgc tgatgctgat tctcttcgta tatctccccg ggaggccagg    540

tcgttaatcg aacaggctga aaaacggcag aaggatgcgc agaacgcaga caagaaggcc    600

gctgatatgc ttgctgaata cgagcgcaga aaaggtattc tggacacccg gttgtcagag    660

ctggaaaaaa atggcggggc agcccttgcc gttcttgatg cacaacaggc ccgtctgctc    720

gggcagcaga cacggaatga cagggccatt tcagaggccc ggaataaact cagttcagtg    780

acggaatcgc ttaacacggc ccgtaatgca ttaaccagag ctgaacaaca gctgacgcaa    840

cagaaaaaca cgcctgacgg caaaacgata gtttcccctg aaaaattccc ggggcgttca    900

tcaacaaatc attctattgt tgtgagcggt gatccgagat ttgccggtac gataaaaatc    960

acaaccagcg cagtcatcga taaccgtgca aacctgaatt atcttctgag ccattccggt   1020

ctggactata aacgcaatat tctgaatgac cggaatccgg tggtgacaga ggatgtggaa   1080

ggtgacaaga aaatttataa tgctgaagtt gctgaatggg ataagttacg gcaaagattg   1140

cttgatgcca gaaataaaat cacctctgct gaatctgcgg taaattcggc gagaaataac   1200

ctcagtgcca gaacaaatga gcaaaagcat gcaaatgacg ctcttaatgc cctgttgaag   1260

gaaaaagaga atatacgtaa ccagctttcc ggcatcaatc agaagatagc ggaagagaaa   1320

agaaaacagg atgaactgaa ggcaacgaaa gacgcaatta atttcacaac agagttcctg   1380

aaatcagttt cagaaaaata tggtgcaaaa gctgagcagt tagccagaga gatggccggg   1440

caggctaaag ggaagaaaat acgtaatgtt gaagaggcat taaaaacgta tgaaaagtac   1500

cgggctgaca ttaacaaaaa aattaatgca aaagatcgtg cagcgattgc cgcagccctt   1560

gagtctgtga agctgtctga tatatcgtct aatctgaaca gattcagtcg ggactggga    1620

tatgcaggaa aatttacaag tcttgctgac tggatcactg agtttggtaa ggctgtccgg   1680

acagagaact ggcgtcctct ttttgttaaa acagaaacca tcatagcagg caatgccgca   1740

acggctcttg tggcactggt cttcagtatt cttaccggaa gcgctttagg cattatcggg   1800

tatggtttac tgatggctgt caccggtgcg ctgattgatg aatcgcttgt ggaaaaagcg   1860

aataagttct ggggtatttc cttcggtatg cattgggtgc gtcaggcccc cgagaaaggt   1920

ctggagtggg tggccggtca gggttactcc taccccctaca cc                     1962
```

<210> SEQ ID NO 9
<211> LENGTH: 7
<212> TYPE: PRT
<213> ORGANISM: Inoviridae

<400> SEQUENCE: 9

```
Thr Leu Thr Thr Lys Leu Tyr
1               5
```

<210> SEQ ID NO 10
<211> LENGTH: 21
<212> TYPE: DNA
<213> ORGANISM: Inoviridae

<400> SEQUENCE: 10

```
acacttacaa caaaacttta c                                               21
```

-continued

<210> SEQ ID NO 11
<211> LENGTH: 633
<212> TYPE: PRT
<213> ORGANISM: Artificial
<220> FEATURE:
<223> OTHER INFORMATION: Fusion peptide

<400> SEQUENCE: 11

```
Met Ser Asp Pro Val Arg Ile Thr Asn Pro Gly Ala Glu Ser Leu Gly
1               5                   10                  15

Tyr Asp Ser Asp Gly His Glu Ile Met Ala Val Asp Ile Tyr Val Asn
            20                  25                  30

Pro Pro Arg Val Asp Val Phe His Gly Thr Pro Pro Ala Trp Ser Ser
        35                  40                  45

Phe Gly Asn Lys Thr Ile Trp Gly Gly Asn Glu Trp Val Asp Asp Ser
    50                  55                  60

Pro Thr Arg Ser Asp Ile Glu Lys Arg Asp Lys Glu Ile Thr Ala Tyr
65                  70                  75                  80

Lys Asn Thr Leu Ser Ala Gln Gln Lys Glu Asn Glu Asn Lys Arg Thr
                85                  90                  95

Glu Ala Gly Lys Arg Leu Ser Ala Ala Ile Ala Ala Arg Glu Lys Asp
            100                 105                 110

Glu Asn Thr Leu Lys Thr Leu Arg Ala Gly Asn Ala Asp Ala Ala Asp
        115                 120                 125

Ile Thr Arg Gln Glu Phe Arg Leu Leu Gln Ala Glu Leu Arg Glu Tyr
    130                 135                 140

Gly Phe Arg Thr Glu Ile Ala Gly Tyr Asp Ala Leu Arg Leu His Thr
145                 150                 155                 160

Glu Ser Arg Met Leu Phe Ala Asp Ala Asp Ser Leu Arg Ile Ser Pro
                165                 170                 175

Arg Glu Ala Arg Ser Leu Ile Glu Gln Ala Glu Lys Arg Gln Lys Asp
            180                 185                 190

Ala Gln Asn Ala Asp Lys Lys Ala Ala Asp Met Leu Ala Glu Tyr Glu
        195                 200                 205

Arg Arg Lys Gly Ile Leu Asp Thr Arg Leu Ser Glu Leu Glu Lys Asn
    210                 215                 220

Gly Gly Ala Ala Leu Ala Val Leu Asp Ala Gln Gln Ala Arg Leu Leu
225                 230                 235                 240

Gly Gln Gln Thr Arg Asn Asp Arg Ala Ile Ser Glu Ala Arg Asn Lys
                245                 250                 255

Leu Ser Ser Val Thr Glu Ser Leu Asn Thr Ala Arg Asn Ala Leu Thr
            260                 265                 270

Arg Ala Glu Gln Gln Leu Thr Gln Gln Lys Asn Thr Pro Asp Gly Lys
        275                 280                 285

Thr Ile Val Ser Pro Glu Lys Phe Pro Gly Arg Ser Ser Thr Asn His
    290                 295                 300

Ser Ile Val Val Ser Gly Asp Pro Arg Phe Ala Gly Thr Ile Lys Ile
305                 310                 315                 320

Thr Thr Ser Ala Val Ile Asp Asn Arg Ala Asn Leu Asn Tyr Leu Leu
                325                 330                 335

Ser His Ser Gly Leu Asp Tyr Lys Arg Asn Ile Leu Asn Asp Arg Asn
            340                 345                 350

Pro Val Val Thr Glu Asp Val Glu Gly Asp Lys Lys Ile Tyr Asn Ala
        355                 360                 365
```

```
Glu Val Ala Glu Trp Asp Lys Leu Arg Gln Arg Leu Leu Asp Ala Arg
    370                 375                 380

Asn Lys Ile Thr Ser Ala Glu Ser Ala Val Asn Ser Ala Arg Asn Asn
385                 390                 395                 400

Leu Ser Ala Arg Thr Asn Glu Gln Lys His Ala Asn Asp Ala Leu Asn
                405                 410                 415

Ala Leu Leu Lys Glu Lys Glu Asn Ile Arg Asn Gln Leu Ser Gly Ile
            420                 425                 430

Asn Gln Lys Ile Ala Glu Glu Lys Arg Lys Gln Asp Glu Leu Lys Ala
        435                 440                 445

Thr Lys Asp Ala Ile Asn Phe Thr Thr Glu Phe Leu Lys Ser Val Ser
    450                 455                 460

Glu Lys Tyr Gly Ala Lys Ala Glu Gln Leu Ala Arg Glu Met Ala Gly
465                 470                 475                 480

Gln Ala Lys Gly Lys Lys Ile Arg Asn Val Glu Glu Ala Leu Lys Thr
                485                 490                 495

Tyr Glu Lys Tyr Arg Ala Asp Ile Asn Lys Lys Ile Asn Ala Lys Asp
            500                 505                 510

Arg Ala Ala Ile Ala Ala Ala Leu Glu Ser Val Lys Leu Ser Asp Ile
        515                 520                 525

Ser Ser Asn Leu Asn Arg Phe Ser Arg Gly Leu Gly Tyr Ala Gly Lys
    530                 535                 540

Phe Thr Ser Leu Ala Asp Trp Ile Thr Glu Phe Gly Lys Ala Val Arg
545                 550                 555                 560

Thr Glu Asn Trp Arg Pro Leu Phe Val Lys Thr Glu Thr Ile Ile Ala
                565                 570                 575

Gly Asn Ala Ala Thr Ala Leu Val Ala Leu Val Phe Ser Ile Leu Thr
            580                 585                 590

Gly Ser Ala Leu Gly Ile Ile Gly Tyr Gly Leu Leu Met Ala Val Thr
        595                 600                 605

Gly Ala Leu Ile Asp Glu Ser Leu Val Glu Lys Ala Asn Lys Phe Trp
    610                 615                 620

Gly Ile Thr Leu Thr Thr Lys Leu Tyr
625                 630
```

<210> SEQ ID NO 12
<211> LENGTH: 1899
<212> TYPE: DNA
<213> ORGANISM: Artificial
<220> FEATURE:
<223> OTHER INFORMATION: Nucleic acid sequence of a fusion peptide

<400> SEQUENCE: 12

```
atgtctgacc ctgtacgtat tacaaatccc ggtgcagaat cgctggggta tgattcagat     60

ggccatgaaa ttatggccgt tgatatttat gtaaaccctc cacgtgtcga tgtctttcat    120

ggtaccccgc ctgcatggag ttccttcggg aacaaaacca tctggggcgg aaacgagtgg    180

gttgatgatt ccccaacccg aagtgatatc gaaaaaaggg acaaggaaat cacagcgtac    240

aaaaacacgc tcagcgcgca gcagaaagag aatgagaata agcgtactga agccggaaaa    300

cgcctctctg cggcgattgc tgcaagggaa aaagatgaaa acacactgaa aacactccgt    360

gccggaaacg cagatgccgc tgatattaca cgacaggagt tcagactcct gcaggcagag    420

ctgagagaat acggattccg tactgaaatc gccggatatg acgccctccg gctgcataca    480

gagagccgga tgctgtttgc tgatgctgat tctcttcgta tatctccccg ggaggccagg    540

tcgttaatcg aacaggctga aaaacggcag aaggatgcgc agaacgcaga caagaaggcc    600
```

-continued

```
gctgatatgc ttgctgaata cgagcgcaga aaaggtattc tggacacccg gttgtcagag    660

ctggaaaaaa atggcggggc agcccttgcc gttcttgatg cacaacaggc ccgtctgctc    720

gggcagcaga cacggaatga cagggccatt tcagaggccc ggaataaact cagttcagtg    780

acggaatcgc ttaacacggc ccgtaatgca ttaaccagag ctgaacaaca gctgacgcaa    840

cagaaaaaca cgcctgacgg caaaacgata gtttcccctg aaaaattccc ggggcgttca    900

tcaacaaatc attctattgt tgtgagcggt gatccgagat ttgccggtac gataaaaatc    960

acaaccagcg cagtcatcga taaccgtgca aacctgaatt atcttctgag ccattccggt   1020

ctggactata aacgcaatat tctgaatgac cggaatccgg tggtgacaga ggatgtggaa   1080

ggtgacaaga aaatttataa tgctgaagtt gctgaatggg ataagttacg gcaaagattg   1140

cttgatgcca gaaataaaat cacctctgct gaatctgcgg taaattcggc gagaaataac   1200

ctcagtgcca gaacaaatga gcaaaagcat gcaaatgacg ctcttaatgc cctgttgaag   1260

gaaaaagaga atatacgtaa ccagctttcc ggcatcaatc agaagatagc ggaagagaaa   1320

agaaaacagg atgaactgaa ggcaacgaaa gacgcaatta atttcacaac agagttcctg   1380

aaatcagttt cagaaaaata tggtgcaaaa gctgagcagt tagccagaga gatggccggg   1440

caggctaaag ggaagaaaat acgtaatgtt gaagaggcat taaaaacgta tgaaaagtac   1500

cgggctgaca ttaacaaaaa aattaatgca aaagatcgtg cagcgattgc cgcagccctt   1560

gagtctgtga agctgtctga tatatcgtct aatctgaaca gattcagtcg ggactggga    1620

tatgcaggaa aatttacaag tcttgctgac tggatcactg agtttggtaa ggctgtccgg   1680

acagagaact ggcgtcctct tttgttaaa acagaaacca tcatagcagg caatgccgca    1740

acggctcttg tggcactggt cttcagtatt cttaccggaa gcgctttagg cattatcggg   1800

tatggtttac tgatggctgt caccggtgcg ctgattgatg aatcgcttgt ggaaaaagcg   1860

aataagttct ggggtattac acttacaaca aaactttac                          1899
```

METHOD OF TREATING VIRUS-INDUCED CANCER

This patent application is a divisional of patent application Ser. No. 11/297,464 filed Dec. 9, 2005, which claims priority to Chinese Patent Application 200410081446.8 filed Dec. 10, 2004, which patent documents are incorporated herein by specific reference in their entirety.

BACKGROUND OF INVENTION

Field of the Invention

As a result of industrial globalization, viral infection by, for example, viral hepatitis, influenza, pneumonia, encephalitis, virus-induced carcinoma and acquired immune deficiency syndrome (AIDS) is becoming an epidemic phenomenon. Virus-induced cancer is becoming a predominant menace to human life. Traditional approaches to the development of antiviral drugs usually attempt to disturb the metabolism of viral genes, interfere with the activity of viral enzymes, or use immunology approaches, such as antibodies and immune factors, to provide viral vaccines. Unfortunately, these drugs often lose their efficacies quickly because a virus can develop resistance through mutation.

Resistance to antiviral therapy has become a major issue in the management of patients with chronic viral infections. Perhaps the best know example is human immunodeficiency virus (HIV), but herpes simplex virus, hepatitis B and C virus, and Epstein-Barr virus exhibit similar capabilities. Accordingly, a need exists for compounds and methods of treating viral infections and drug resistant virus.

According to the most recent data available from the American Cancer Society, cancer is the second leading cause of death in the United States trailing only heart disease. Nearly one quarter of all deaths in the United States are caused by cancer.

Many types of chemotherapeutic agents have been shown to be effective against cancers and tumor cells, but not all types of cancers and tumors respond to these agents. Unfortunately, many of these agents also destroy normal cells.

Despite advances in the field of cancer treatment, the leading therapies to date are surgery, radiation and chemotherapy. Chemotherapeutic approaches work best on cancers that are metastasized or ones that are particularly aggressive, i.e., ones whose cells are rapidly dividing. Ideally cytotoxic agents would have specificity for cancer and tumor cells while not affecting normal cells.

The development of materials that would specifically target cancer cells is extremely desirable. In addition, materials that are cytotoxic to cancer cells while exerting mild effects on normal cells would also desirable.

Accordingly, new and effective cancer treatments are needed to treat subjects that have, or will develop, cancer.

SUMMARY OF THE INVENTION

The instant invention is based on the discovery that a bifunctional molecule comprising a targeting agent and a channel-forming moiety can selectively kill cells, e.g., cancer cells. The invention provides a novel class of preferred compounds that kill cells. Accordingly, in one aspect, the instant invention provides a molecule comprising a targeting agent attached to a channel-forming moiety. In one embodiment, the molecule is a polypeptide.

In certain embodiments, the channel-forming moiety is a channel-forming peptide, a channel-forming domain, or fragment thereof. For example, the channel-forming peptide can be α-hemolysin, delta toxin, diphtheria toxin, anthrax toxin, and E1 family colicin. In particular embodiments the colicin is E1, Ia, Ib, A, K or N. In one particular embodiment, the colicin is colicin Ia.

In a related embodiment, the channel-forming fragment is a channel-forming colicin comprising amino acid residues from about 1 to about amino acid 626 of colicin Ia (SEQ ID NO:1) having the nucleic acid sequence of SEQ ID NO:2. In a specific embodiment, the channel-forming domain comprises amino acid residues 451-626 (SEQ ID NO:3) having the nucleic acid sequence of SEQ ID NO:4.

In specific embodiments, the targeting agent is selected from the group consisting of a ligand, an antibody, an antibody fragment, a reconstituted antibody mimetic, and a phage segment.

In one embodiment the targeting agent is C-terminal to the channel-forming moiety. In an alternative embodiment, the targeting agent is N-terminal to the channel-forming moiety.

In another embodiment, the targeting agent is an antibody or fragment thereof, or a reconstituted antibody mimetic.

In a related embodiment, the antibody, a fragment thereof, or a reconstituted antibody mimetic is a specific for a polypeptide expressed by a cell, e.g., a cancer cell. In a related embodiment, the antibody is an engineered antibody variant or a reconstituted antibody mimetic.

In one aspect, the invention provides a polypeptide comprising an antibody and a channel-forming colicin, or a channel-forming fragment thereof, of colicin. In a related embodiment, the colicin comprises residues 1-626 of colicin Ia. In a specific embodiment, the channel-forming domain comprises residues 451-626 of colicin Ia.

In one aspect, the invention provides a polypeptide comprising the Epstein-Barr virus gp350/220 envelope glycoprotein engineered antibody variant, or a reconstituted antibody mimetic, and a channel-forming domain of colicin. In a specific embodiment, the channel-forming domain of colicin comprises residues from about residue 1 to about residue 626 of colicin Ia. Ia specific embodiment, the channel-forming domain comprises amino acid residues 451-626.

In a related embodiment, the polypeptides of the invention may have one or more non-natural amino acid residues, e.g., amino acid analogs, or mimetics.

In a specific embodiment, the non-natural amino acid residues are D-isomers of natural amino acid residues.

In another aspect, the invention provides a nucleic acid molecule that encodes a polypeptides of the invention.

In a related embodiment, the invention provides a vector, e.g., an expression vector, comprising a nucleic acid molecule that encodes a polypeptide of the invention.

In a related embodiment, the invention provides a host cell comprising a vector of the invention. In a specific embodiment, the host cell is a bacterial cell, e.g., *E. coli*, or a yeast or mammalian host cell.

In another aspect, the invention further provides methods of producing the polypeptide of the invention. The methods comprise the steps of culturing the host cells of the invention such that the polypeptides are produced. In a further embodiment, the methods of the invention may involve purifying said polypeptide.

In another aspect, the invention provides a method of producing a molecule of the invention wherein the targeting agent and the channel-forming moiety are produced separately and covalently linked after production. In a related embodiment, the channel-forming moiety and/or the targeting agent are produced recombinantly.

In another aspect, the invention provides methods of treating a subject having cancer, comprising administering to the subject an effective amount of a polypeptide comprising an targeting agent and a channel-forming moiety thereby treating the subject.

In a related embodiment, the targeting agent is selected from the group consisting of an antibody, a fragment thereof, an engineering antibody variant, and a reconstituted antibody mimetic. In a specific embodiment, the reconstituted antibody mimetic or variants was a complementarity determining regions pair ($V_H$CDR1 and $V_L$CDR3) selected from the antibody fragment against EBV gp350/220 envelope glycoprotein.

In one embodiment, the channel-forming moiety is selected from the group consisting of α-hemolysin, delta toxin, diphtheria toxin, anthrax toxin, and E1 family colicin, or a fragment thereof. In specific embodiments the colicin, or the fragment of colicin, is selected from the group consisting of E1, Ia, Ib, A, K or N. In one particular embodiment, the colicin is colicin Ia. In further particular embodiments, the fragment of colicin Ia comprises amino acid residues 1-626 or 451-626.

In another aspect, the invention provides a method of treating a subject having a viral associated cancer comprising administering to the subject an effective amount of a polypeptide comprising an targeting agent and a channel-forming moiety thereby treating said subject.

BRIEF DESCRIPTION OF THE DRAWINGS

FIG. 3A is a CCD image of cells treated with stock solution of pheromonicin as a control. FIG. 3B is a CCD image of cells treated with 50 μg/ml of Ph-CNCV. Cells are stained with 50 nM acridinorange/600 nM propidium iodide. Cellular swelling, mitochondria degeneration and cell rupture were detected along with the Ph-CNCV.

FIG. 4A is a CCD image of cells treated with stock solution of pheromonicin as a control. FIG. 4B is a CCD image of cells treated with 50 μg/ml of Ph-EBV. Cells are stained with 50 nM acridinorange/600 nM propidium iodide. Cellular swelling, mitochondria degeneration and cell rupture were detected along with the Ph-EBV.

FIG. 5A is a CCD image of cells treated with stock solution of pheromonicin as a control. FIG. 5B is a CCD image of cells treated with 50 μg/ml of Ph-EBV. Cells are stained with 50 nM acridinorange/600 nM propidium iodide. Ph-EBV has no effects on EBV-uninfected lymphoma cells.

FIG. 6A is a CCD image of cells treated with stock solution of pheromonicin as a control. FIG. 6B is a CCD image of cells treated with 50 μg/ml of Ph-EBV. Cells are stained with 50 nM acridinorange/600 nM propidium iodide. Cellular swelling, mitochondria degeneration and cell rupture were detected along with the Ph-EBV.

FIG. 7A is a CCD image of cells treated with stock solution of pheromonicin as a control. FIG. 7B is a CCD image of cells treated with 50 μg/nil of Ph-EBV. Cells are stained with 50 nM acridinorange/600 nM propidium iodide. Ph-EBV has no effects on hepatoma cells.

FIG. 8A is a CCD image of cells treated with stock solution of pheromonicin as a control. FIG. 8B is a CCD image of cells treated with 50 μg/ml of Ph-EBV. Cells are stained with 50 nM acridinorange/600 nM propidium iodide. Ph-EBV has no effects on fibroblast cells.

FIG. 9B is a CCD image of cells treated with 50 μg/ml of Ph-EBV. Cells are stained with 50 nM acridinorange/600 nM propidium iodide. Ph-EBV has no effects on endothelium cells.

FIG. 10A depicts exposed xenografts after 16-day intraperitoneal Ph-EBV stock solution treatment (0.5 ml/mouse/day). FIG. 10B depicts exposed xenografts after 16-day intraperitoneal Ph-EBV treatment ((350 μg/mouse/day)). FIG. 10C depicts a 400× microscope image of EBV-uninfected xenograft in stock solution-treated mouse. FIG. 10D depicts a 400× microscope image of EBV-infected xenograft in stock solution-treated mouse. FIG. 10E depicts a 400× microscope image of EBV-uninfected xenograft in Ph-EBV-treated mouse. FIG. 10F depicts a 400× microscope image of EBV-infected xenograft in Ph-EBV-treated mouse.

FIG. 11A-K shows the killing effects of Ph-EBV against solid tumors. FIG. 11A depicts an exposed Burkitt Lymphoma xenograft after 20-day intraperitoneal Ph-EBV stock solution treatment (0.5 ml/mouse/day). FIG. 11B depicts a 100× microscope image of the xenograft. FIG. 11C depicts exposed Burkitt Lymphoma xenograft after 20-day intraperitoneal Ph-EBV treatment (350 μg/mouse/day). FIG. 11D depicts a 100× microscope image of the xenograft. FIG. 11E depicts exposed AIDS related body cavity based lymphoma xenograft after 20-day intraperitoneal Ph-EBV stock solution treatment (0.5 ml/mouse/day). FIG. 11F depicts a 100× microscope image of the xenograft. FIG. 11G depicts an exposed AIDS related body cavity based lymphoma xenograft after 20-day intraperitoneal Ph-EBV treatment (350 μg/mouse/day). FIG. 11H depicts a 100× microscope image of the xenograft. FIG. 11I depicts exposed nasopharyngeal cancer xenograft after 20-day intraperitoneal Ph-EBV stock solution treatment (0.5 ml/mouse/day). FIG. 11J depicts a 100× microscope image of the xenograft. FIG. 11K depicts exposed nasopharyngeal cancer after 20-day intraperitoneal Ph-EBV treatment (350 μg/mouse/day).

FIG. 12A depicts the FITC-labeled Ph-EBV in vivo image at 1 hour after intraperitoneal Ph-EBV given. FIG. 12B depicts the image at 2 hours after intraperitoneal Ph-EBV given. FIG. 12C depicts the image at 3 hours after intraperitoneal Ph-EBV given. FIG. 12D depicts the image at 6 hours after intraperitoneal Ph-EBV given. FIG. 12E depicts the image at 3 hours after intraperitoneal HB-168 given. FIG. 12F depicts the image at 6 hours after intraperitoneal HB-168 given. FIG. 12G depicts the image at 6 hours after intraperitoneal Ph-SA given.

FIG. 13A depicts a 100× microscope image of liver. FIG. 13B depicts a 100× microscope image of intestine. FIG. 13C depicts a 100× microscope image of kidney. FIG. 13D depicts 100× microscope image of spleen.

DETAILED DESCRIPTION

Figure 1:
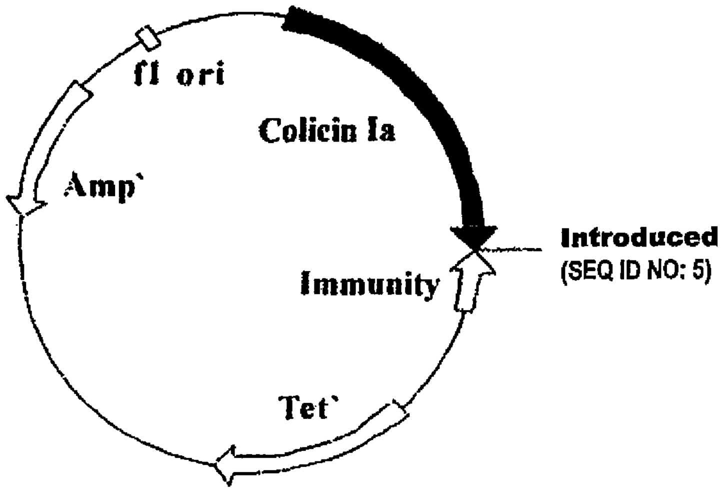
FIG. 1 schematically depicts the structure of a recombinant plasmid that contains a complementarity determining region pair as a targeting domain which is selected from a FIB-168 monoclonal antibody fragment against Epstein-Barr virus gp350/220 envelope antigen and linked to a VHCDR1/VHCDR2 linker of that fragment FIG. 2 schematically depicts the structure of a recombinant plasmid that contains a targeting domain derived from bacteriophage M13.
Figure 2:
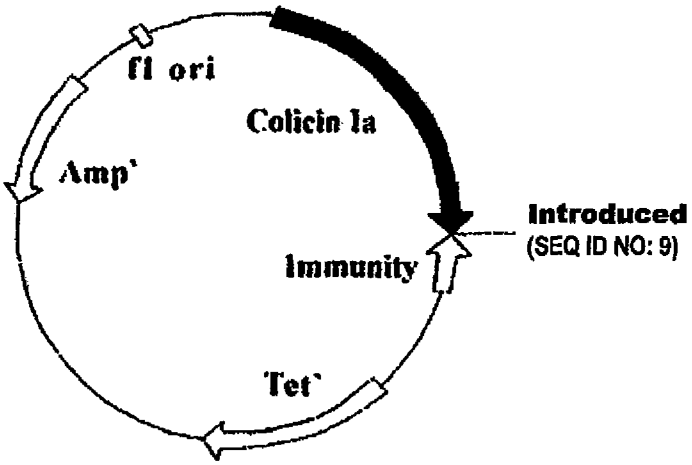

Before further description of the invention, certain terms employed in the specification, examples and appended claims are, for convenience, explained here.

The term "targeting agent" is intended to include molecules, e.g., small molecules, peptides, and polypeptides, that specifically recognize given types of cells. These agents can bind to a polypeptide or carbohydrate expressed by a cell, e.g., on the surface of a cancer cell. Nonlimiting examples of the targeting agents of the invention include antibodies, engineered antibody variants, reconstituted antibody mimetics, fragments of antibodies, single domain antibodies, phage segments or small molecules. These targeting agents can recognize a polypeptide expressed by a cancerous cell or a viral peptide expressed by a cancerous cell. Exemplary, nonlimiting, cell produced polypeptides include Her2, estrogen receptor, progesterone receptor, STEAP, carcinoembryonic antigen, prostate carcinoma tumor antigen and T-antigen. In further embodiments, the targeting agent may be a ligand that binds to a receptor expressed by a cancer cell, e.g., estrogen receptor.

The term "channel-forming moiety" is intended to include transmembrane polypeptides that are capable of inserting into a lipid bilayer thereby creating a gating passageway, from inside of the cell compartment to outside of the cell compartment. In preferred embodiments, the gating passageway is not specific in term of what is permitted to pass through the channel. Exemplary channel-forming moieties are polypeptides that naturally form channels in lipid bilayers, i.e., α-hemolysin, delta toxin, diphtheria toxin, anthrax toxin, and E1 family colicin, Channel-forming moieties can also be fragments of naturally occurring polypeptides that retain the ability to insert into a lipid bilayer and form a channel. One of skill in the art would be able to isolate many fragments of naturally occurring polypeptides that have the ability to form a channel. Those channel-forming fragments are intended to be used in the methods and compositions of the instant invention.

The term "antibody" as used herein refers to immunoglobulin molecules and immunologically active portions of immunoglobulin molecules, i.e., molecules that contain antigen binding sites which specifically bind (immunoreacts with) an antigen. Nonlimiting examples of immunologically active portions of immunoglobulin molecules include F(ab) and $F(ab')_2$ fragments which can be generated by treating the antibody with an enzyme, such as pepsin.

The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope. A monoclonal antibody composition thus typically displays a single binding affinity for a particular protein with which it immunoreacts.

The term "reconstituted antibody mimetic" refers to a targeting agent comprising one or more antibody complementarity determining regions (CDRs) covalently linked to, for example, a polypeptide linker. For example, $V_H$CDR1, $V_H$CDR2, $V_H$CDR3, $V_L$CDR1, $V_L$CDR2, or $V_L$CDR3 regions from light or heavy chains of an antibody fragment may be covalently attached to confer binding affinity, i.e., sufficient binding ability to allow the molecules of the invention to target a cell and allow for insertion of the channel-forming domain into the lipid bilayer. The CDRs may be linked together directly, by using random peptides, or by using the natural linking peptides present in antibody heavy or light chains. The CDR regions are generally from an antibody that specifically recognizes an epitope presented by a target cell. In a specific embodiment, the reconstituted antibody mimetic or variants are a complementarity determining region pair ($V_H$CDR1 and $V_L$CDR3) selected from the antibody fragment linked by natural $V_H$CDR1/$V_H$CDR2 linker.

The terms "protein" and "polypeptide" are used interchangeably herein. The term "peptide" is used herein to refer to a chain of two or more amino acids or amino acid analogs (including non-naturally occurring amino acids and amino acid analogues), with adjacent amino acids joined by peptide (—NHCO—) bonds. Thus, peptides in accordance with the invention include oligopeptides, polypeptides, proteins, and peptidomimetics.

The term "fragment" refers to any portion of a natural, recombinant or synthetic polypeptide. A fragment can be made synthetically, enzymatically, or recombinantly.

The term "pharmaceutical composition" includes preparations suitable for administration to mammals, e.g., humans. When the compounds of the present invention are administered as pharmaceuticals to mammals, e.g., humans, they can be given as is or as a pharmaceutical composition containing, for example, 0.1 to 99.5% of active ingredient in combination with a pharmaceutical acceptable carrier. Pharmaceutical compositions of the current invention may further contain, for example a biocide, antimicrobial, or antibiotic.

As used herein, the term "cell proliferative disorder" is intended to include diseases or disorders characterized by abnormal cell growth, e.g., cancer.

As used herein, the term "abnormal cell growth" is intended to include cell growth which is undesirable or inappropriate. Abnormal cell growth also includes proliferation which is undesirable or inappropriate (e.g., unregulated cell proliferation or undesirably rapid cell proliferation). Abnormal cell growth can be benign and result in benign masses of tissues or cells, or benign tumors. Abnormal cell growth can also be malignant and result in malignancies, malignant masses of tissues or cells, or malignant tumors. Many art-recognized conditions and disorders are associated with malignancies, malignant masses, and malignant tumors including cancer and carcinoma.

As used herein, the term "tumor" is intended to encompass both in vitro and in vivo tumors that form in the body. Tumors may be associated with benign abnormal cell growth (e.g., benign tumors) or malignant cell growth (e.g., malignant tumors).

"Cancer" includes a malignant neoplasm characterized by deregulated or uncontrolled cell growth. The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site pf the original tumor). Cancer may develop in, for example, the following tissues: larynx, prostate, stomach, skin, oral cavity, pharynx, esophagus, liver, lung, head, neck, bronchus, pancreas, small intestine, colon, rectum, breast, bladder, uterus, brain, lymph system, blood, ovaries, kidneys, or soft tissue.

The histological features of cancer are summarized by the term "Anaplasia". Malignant neoplasms often contain numerous mitotic cells. These cells are typically abnormal. Such mitotic aberrations account for some of the karyotypic abnormalities found in most cancers. Bizarre multinucleated cells are also seen in some cancers, especially those which are highly anaplastic. "Dysplasia" refers to a pre-malignant state in which a tissue demonstrates histologic and cytologic features intermediate between normal and anaplastic. Dysplasia is often reversible.

"Anaplasia" refers to the histological features of cancer. These features include derangement of the normal tissue architecture, the crowding of cells, lack of cellular orientation termed dyspolarity, cellular heterogeneity in size and shape termed "pleomorphism." The cytologic features of anaplasia include an increased nuclear-cytoplasmic ratio (the nuclear-cytoplasmic ratio can be over 50% for malignant cells), nuclear pleomorphism, clumping of the nuclear chromatin along the nuclear membrane, increased staining of the nuclear chromatin, simplified endoplasmic reticulum, increased free ribosomes, pleomorphism of mitochondria, decrease in size and number of organelles, enlarged and increased numbers of nucleoli, and sometimes the presence of intermediate filaments.

"Neoplasis" or "neoplastic transformation" is the pathologic process that results in the formation and growth of a neoplasm, tissue mass, or tumor. Such process includes uncontrolled cell growth, including either benign or malignant tumors. Neoplasms include abnormal masses of tissue, the growth of which exceeds and is uncoordinated with that of the normal tissues and persists in the same excessive manner after cessation of the stimuli which evoked the change. Neoplasms may show a partial or complete lack of structural organization and functional coordination with the normal tissue, and usually form a distinct mass of tissue.

Neoplasms tend to morphologically and functionally resemble the tissue from which they originated. For example, neoplasms arising within the islet tissue of the pancreas resemble the islet tissue, contain secretory granules, and secrete insulin. Clinical features of a neoplasm may result from the function of the tissue from which it originated.

By assessing the histologic and other features of a neoplasm, it can be determined whether the neoplasm is benign or malignant. Invasion and metastasis (the spread of the neoplasm to distant tissue) are definitive attributes of malignancy. Despite the fact that benign neoplasms may attain enormous size, they remain discrete and distinct from the adjacent non-neoplastic tissue. Benign tumors are generally well circumscribed and round, have a capsule, and have a grey or white color, and a uniform texture. By contrast, malignant tumor generally have fingerlike projections, irregular margins, are not circumscribed, and have a variable color and texture. Benign tumors grow by pushing on adjacent tissue as they grow. As the benign tumor enlarges it compresses adjacent tissue, sometimes causing atrophy. The junction between a benign tumor and surrounding tissue may be converted to a fibrous connective tissue capsule allowing for easy surgical remove of benign tumors. By contrast, malignant tumors are locally invasive and grow into the adjacent tissues usually giving rise to irregular margins that are not encapsulated making it necessary to remove a wide margin of normal tissue for the surgical removal of malignant tumors. Benign neoplasms tends to grow more slowly than malignant tumors. Benign neoplasms also tend to be less autonomous than malignant tumors. Benign neoplasms tend to closely histologically resemble the tissue from which they originated. More highly differentiated cancers, cancers that resemble the tissue from which they originated, tend to have a better prognosis than poorly differentiated cancers. Malignant tumors are more likely than benign tumors to have an aberrant function (i.e. the secretion of abnormal or excessive quantities of hormones).

The term "subject" includes organisms which can suffer from cancer. The term subject includes mammals, e.g., horses, monkeys, bears, dogs, cats, mice, rabbits, cattle, squirrels. Rats, and, preferably, humans.

Molecules of the Invention

The present invention provides molecules, e.g., fusion molecules, comprising a targeting agent and a channel-forming moiety. The targeting agent can be a small molecule, peptide, e.g., an antibody, or peptidomimetic. Accordingly, the polypeptides of the invention are threefold: a polypeptides comprising a targeting agent, a polypeptide comprising a channel-forming moiety, and a polypeptide comprising a targeting agent and a channel-forming moiety.

Targeting agents of the invention serve to bring a fusion molecule in close proximity to the surface of a cell, e.g., a cancer cell.

One class of targeting agents of the invention are small molecules that bind to receptors expressed on the surface of an cell.

A second class of targeting agents are peptides, or polypeptides, that specifically bind to proteins on a cell surface, e.g., an antibody. In one embodiment, the peptides are molecules that bind to a cell surface receptor. In another embodiment, the peptides are molecules that bind to a cell surface antigen, e.g., antibodies, reconstituted antibodies, ScFvs, or fragments thereof.

A preferred polypeptide that is capable of acting as a targeting agent is an antibody or a reconstituted antibody mimetic. Antibody fragments, e.g., Fab fragments or reconstituted antibody mimetics, preferably retain the ability to specifically recognize a target cell. A reconstituted antibody mimetic derived from a complementarity determining regions pair ($V_H$CDR1 and $V_L$CDR3) selected from the antibody fragment linked by natural $V_H$CDR1/$V_H$CDR2 linker is capable of acting as such a targeting agent.

Reconstituted antibody mimetic molecules that specifically recognize an antigen on the cell surface of a cell, e.g., a viral antigen or cancer cell marker, can be used as the targeting agent. Specifically, reconstituted antibody mimetic molecules that recognize viral peptides, e.g., herpes virus particles or channel-forming domains thereof, can be used as a channel-forming polypeptide of the invention. Exemplary, non-limiting mimetic molecules that are contemplated for use in the methods and compositions of the invention are the variants of complementarity determining regions pairs selected from the antibody fragment against Epstein-Barr virus gp350/220 envelope glycoprotein.

Another preferred class of targeting agents are antibodies against target cell surface polypeptides that are differentially expressed in cancer cells. For example, a number of polypeptides are known that are expressed at higher levels in cancer cells than in normal non-cancerous cells. Exemplary polypeptides that are differentially expressed in one or more cancerous tissues are Her2, estrogen receptor, progesterone receptor, STEAP, carcinoembryonic antigen, prostate carcinoma tumor antigen and T-antigen.

Nucleic Acid Molecules of the Invention

Another aspect of the invention pertains to vectors, preferably expression vectors, containing a nucleic acid molecule encoding a polypeptide of the invention (or a portion thereof). As used herein, the term "vector" refers to a nucleic acid molecule capable of transporting another nucleic acid molecule to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid molecule of the invention in a form suitable for expression of the nucleic acid molecule in a host cell, which means that the recombinant expression vectors include one or more regulatory sequences, selected on the basis of the host cell to be used for expression, which are operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Acedemic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to produce proteins or peptides, including fusion proteins or peptides, encoded by nucleic acids as described herein (e.g., polypeptides comprising a targeting domain and a channel-forming polypeptide).

The recombinant expression vectors of the invention can be designed for expression of the polypeptides of the invention in prokaryotic or eukaryotic cells. For example, the polypeptides can be expressed in bacterial cells such as *E. coli*, insect cells (using baculovirus expression vector) yeast cells or mammalian cells. Suitable host cells are discussed further in Goeddel; *Gene Expression Technology: Methods in Enzymology* 185, Acedemic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, including Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Acedemic Press, San Diego, Calif. (1990) 69-89). Target gene expression from the pTrc vector relies on host RNA polymerase transcription from a hybrid trp-lac fusion pomoter. Target gene expression from the pET 11d vector relies on transcription from a T7 gn10-lac fusion promoter mediated by a coexpressed viral RNA polymerase (T7gn1). This viral polymerase is supplied by host strains BL21 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Acedemic Press, San Diego, Calif. (1990) 119-128). Another strategy is to alter the nucleic acid sequences of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

In another embodiment, the expression vector is a yeast expression vector. Examples of vectors for expression in yeast *S. cerivisae* include pYepSec1 (Baldari, et al., (1987) *EMBO J.* 6:229-234), pMFa (Kurjan and Herskowitz, (1982) *Cell* 30:933-943), pJRY88 (Schultz et al., (1987) *Gene* 54:113-123), pYES2 (Invitrogen Corp. San Diego, Calif.), and picZ (Invitrogen Corp. San Diego, Calif.).

Alternatively, the polypeptides can be expressed in insect cells using baculovirus expression vectors. Baculovirus vectors available for expression of proteins in cultured insect cells (e.g., Sf9 cells) include the pAc series (Smith et al.

(1983) *Mol. Cell Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T, Molecular Cloning: *A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in art. Non-limiting examples of suitable tissue-specific promoters include the albumin promoter (live-specific; Pinkert et al. (1987) *Genes Dev.* 1:268-277), lymphoid-specific promoters (Calame and Eaton (1988) *Adv. Immunol.* 43:235-275), in particular promoters of T-cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter, Byrne and Ruddle (1989) *Proc. Natl. Acad. Sci. USA* 86:5473-5477), pancreas-specific promoters (e.g., milk whey promoter; U.S. Pat. No. 4,873,316 and European Application Publication No. 264,166). Developmentally-regulated promoters are also encompassed, for example the murine box promoters (Kessek and Gruss (1990) *Science* 249:374-379) and the α-fetoprotein promoter (Campes and Tilghman (1989) *Genes Dev.* 3:537-546).

Another aspect of the invention pertains to host cells into which a nucleic acid molecule encoding a polypeptide of the invention is introduced within a recombinant expression vector or a nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a polypeptide of the invention can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or eletroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. A nucleic acid encoding the polypeptide of the invention can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) the polypeptides of the invention. Accordingly, the invention further provides methods for producing polypeptides using the host cells of the invention. In one embodiment, the method comprises culturing the host cell of the invention (into which a recombinant expression vector encoding a polypeptide of the invention has been introduced) in a suitable medium such that a polypeptide of the invention is produced. In another embodiment, the method further comprises isolating the polypeptide from the medium or the host cell.

The host cells of the invention can also be used to produce non-human transgenic animals. For example, in one embodiment, a host cell of the invention is a fertilized oocyte or an embryonic stem cell into which coding sequences have been introduced. Such host cells can then be used to create non-human transgenic animals in which exogenous sequences have been introduced into their genome or homologous recombinant animals in which endogenous sequences have been altered. As used herein, a "transgenic animal" is a non-human animal, preferably a mammal, more preferably a rodent such as rat or mouse, in which one or more of the cells of the animal includes transgene. Other examples of transgenic animals include non-human primates sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a nucleic acid into the male pronuclei of a fertilized oocyte, e.g., by microinjection, retroviral infection, and allowing the oocyte to develop in a pseudopregnant female foster animal. The cDNA sequence encoding a polypeptide of the invention can be introduced as a transgene into the genome of a non-human animal. Intronic sequences and polyadenylation signals can also be included in the transgene to increase the efficiency of expression of the transgene. A tissue-specific regulatory sequence(s) can be operably linked to a transgene to direct expression of a protein to particular cells. Methods for generating transgenic animals via embryo manipulation and microinjection, particularly animals such as mice, have become conventional in the art and are described, for example, U.S. Pat. No. 4,873,191 by Wagner et al. and in Hogan, B., Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of a transgene in its genome and/or expression of mRNA in tissues or cells of the animals. A transgenic founder animal can then be used to breed additional animals carrying the transgene. Moreover, transgenic animals carrying a transgene encoding a protein can further be bred to other transgenic animals carrying other transgenes.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810-813 and PCT International Publication Nos. WO97/07668 and WO97/07669. In brief, a cell, e.g., a somatic cell, from the transgenic animal can be isolated and induced to exit the growth cycle and enter Go phase. The quiescent cell can then be fused, e.g., through the use of electrical pulses, to enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

Methods of Making the Molecules of the Invention

As described above, molecules of the invention may be made recombinantly using the nucleic acid molecules, vectors, and host cells described above.

Alternatively, the targeting moiety can be made synthetically, or isolated from a natural source and linked to the channel-forming moiety using methods and techniques well known to one of the skill in the art.

Further, to increase the stability or half life of the compounds of the invention, the peptides may be made, e.g., synthetically or recombinantly, to include one or more peptide analogs or mimetics. Exemplary peptides can be synthesized to include D-isomers of the naturally occurring amino acid residues to increase the half life of the molecule when administered to a subject.

Pharmaceutical Compositions

The molecule of the invention (also referred to herein as "active compounds") of the invention can be incorporated into pharmaceutical compositions suitable for administration. Such compositions typically comprise the active compound and a pharmaceutically acceptable carrier. As used herein the language "pharmaceutically acceptable carrier" is intended to include any and all solvents, dispersion media, coatings, antibacterial and anitfungal agents, isotonic and absorption delaying agents, and the like, compatible with pharmaceutical administration. The use of such media and agents for pharmaceutically active substances is well known in the art. Except in so far as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. PH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered salines (PBS). In all cases, the composition must be sterile and should be fluid to the extent that easy syringability exists. It must be stable under the conditions of manufacture and storage and must be preserved against the contaminating action of microorganism such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredients plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of following ingredients, or compounds of a similar nature: a binder such as microcrystalline cellulose, gum tragacanth or gelatin; an excipient such as starch or lactose, a disintegrating agent such as alginic acid, Primogel, or corn starch, a lubricant such as magnesium stearate or Sterotes; a glidant such as colloidal silicon dioxide; a sweetening agent such as sucrose or saccharin; or flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal spray or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as controlled release formulation, including implants and microencapsulated delivery systems. Biodegradable, biocompatible polymers can be used, such as ethylene vinyl acetate, polyanhydrides, polyglycolic acid, collagen, polyorthoesters, and polyacetic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ration between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially form cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

Methods of Treatment

The present invention provides therapeutic methods of treating a subject having a cell proliferative disorder. In certain embodiments, the cell proliferative disorder is cancer. In a specific embodiment, the cell proliferative disorder is a viral associated cancer.

As used herein, the term "treating" refers to the administration of a therapeutically effective amount of an active compound to a subject, for prophylactic and/or therapeutic purposes. The term "administration" includes delivery to a subject, e.g., by any appropriate method which serves to deliver the drug to the site of the cancer. Administration of the drug can be, e.g., oral, intravenous, or topical (as described in further detail below).

In a one embodiment, a subject having a cell proliferative disorder is treated with an effective amount of an active compound of the invention such that the cell proliferative disorder is treated. In a specific embodiment, the subject that is being treated has cancer.

In one embodiment, a composition of the invention is administered to a subject in combination with additional agents, e.g., other compositions useful for treating cell proliferative disorders.

The composition of the invention can be administered to a subject in need of treatment in an effective amount using the pharmaceutical compositions described herein.

This invention is further illustrated by the following examples which should not be construed as limiting. The contents of all references, patents and published patent applications cited throughout this application are incorporated herein by reference.

EXEMPLIFICATION

Example 1

Cytocidal Effects on Burkitt Lymphoma Cells

A fusion peptide that has been identified as pheromonicin-EBV (Ph-EBV) was created incorporating a peptide chain of colicin Ia with a reconstituted mimetic of $V_H$CDR1/$V_L$CDR3 pair of ATCC HB-168 monoclonal IgG fragment, two CDR linked to the HB-168 IgG $V_H$CDR1/$V_H$CDR2 linker, SFG-MHWVRQAPEKGLEWVAGQGY SYPYT (SEQ ID NO:5) having the nucleic acid sequence of SEQ ID NO:6, and was introduced following C-terminus of colicin Ia (1626) to form a 654 residue peptide (SEQ ID NO:7) having the nucleic acid sequence of SEQ ID NO:8.

A second fusion peptide that has been denominated as pheromonicin-CNCV (Ph-CNCV), was created by incorporating a peptide chain of colicin Ia with a phage segment of filamentous bacteriophage M13, TLTTKLY (SEQ ID NO:9) having the nucleic acid sequence of SEQ ID NO:10, and was introduced following the C-terminus of colicin Ia (1626) to form a 633 residue peptide (SEQ ED NO:11) having the polynucleotide sequence of SEQ ID NO:12.

Ph-EBV and Ph-CNCV both demonstrated cytocidal effects on EBV-infected tumor cells (Ragi cell) in vitro (FIGS. 3, 4 and 6, respectively). In contrast, neither peptide demonstrated cytocidal effects on normal mammalian cells and malignant cells with no virus gene transferred (FIGS. 5, 7, 8, and 9, respectively).

Human Burkitt malignant lymphoma cell strain ATCC CCL-86 (Epstein-Barr virus positive) and human acquired immunodeficiency syndrome (AIDS) related body cavity based lymphoma cell strain ATCC CRL-2230 (Epstein-Barr virus and Kaposi sarcoma associated herpesvirus positive) were used to test in vitro cell growth inhibition. Assays were performed in Falcon 3046 six-well tissue culture plate containing 3 ml of PRMI 1640 medium, at 37° C. and monitored with a Olympus IX-71 inverted microscope/colored CCD every 24 hours. After approximately 12 hours the cell density reached about $10^5$ cell/ml. Test agents were added once cell densities reached $10^5$ cell/ml. Cell death was monitored and 50 nM acridinorange/600 nM propidium iodide fluorescent dyes were added 72 hours after the test agents were added.

Figure 3A:
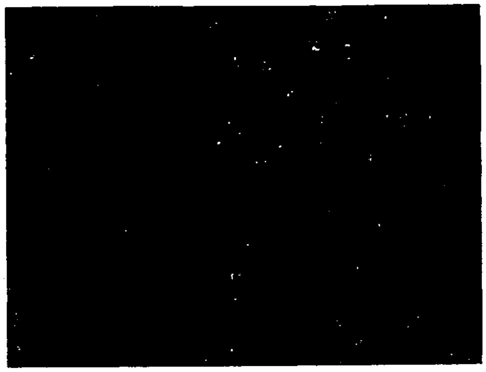
FIG. 3A-B depict images of EBV-infected Burkitt's malignant lymphoma cells after 72 hours of treatment with Ph-CNCV.
Figure 3B:
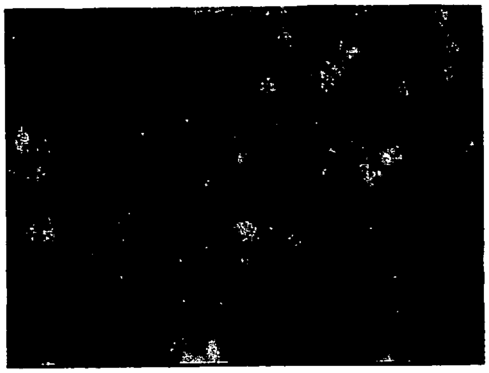
Figure 4A:
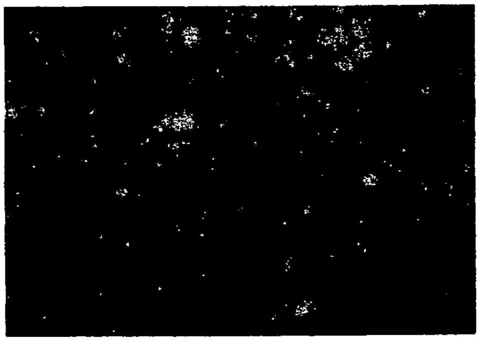
FIG. 4A-B depict images of human EBV-infected Burkitt's malignant lymphoma cells after 72 hours of treatment with Ph-EBV.
Figure 4B:

Ph-EBV and Ph-CNCV were added to human Burkitt malignant lymphoma cell cultures at concentration of 50 μg/ml (FIGS. 3B and 4B). An equivalent amount of PBS stock solution (pH7.4, 10 mM PBS, 0.2M NaCl)(FIGS. 3A and 4A) as controls. 50 μg/ml Ph-EBV killed about 60-70% and 50 μg/ml Ph-CNCV killed about 30-40% of the lymphoma cells after 72 hours of incubation.

To assess the potential targeting efficiency of Ph-EBV and Ph-CNCV to normal and malignant mammalian cells, ATCC CRL-1648 human Burkitt malignant lymphoma cells (Epstein-Barr virus negative) ATCC 3T3 mouse fibroblast, ECV-304 human umbilical cord vein endothelium and SMMC-7721 human hepatocellular cancer cells (Institute of Biochemistry & Cell Biology, Shanghai, Chinese Academy of Science) were incubated with Ph-Ph-EBV and Ph-CNCV 200 μg/ml respectively over 96 hours. No difference in cell counts was observed. Further, cell morphology and lactate dehydrogenase levels in cultured cells were consistent when compared to untreated controls. The data indicate that two anticancer peptides present good targeting efficiency to malignant cells with virus antigen presented on their cell membranes.

Example 2

In Vivo Elimination Effects Against EBV-Associated Human Tumor Xenografts in Immunodeficiency Mice To assess the effects of pheromonicin in vivo, solid tumor models were set up in two species of immunodeficiency mice by inoculation either EBV-infected or uninfected human tumor cells to identify whether pheromonicin inhibited the proliferation of solid tumors.

Figure 10A:
FIG. 10A-F shows the killing effects of Ph-EBV against xenograft inoculated with tumor cells in immunodeficiency mice as solid tumor models.
Figure 10B:
Figure 10C:
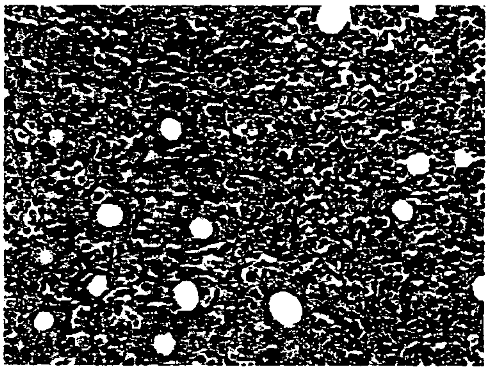
Figure 10D:
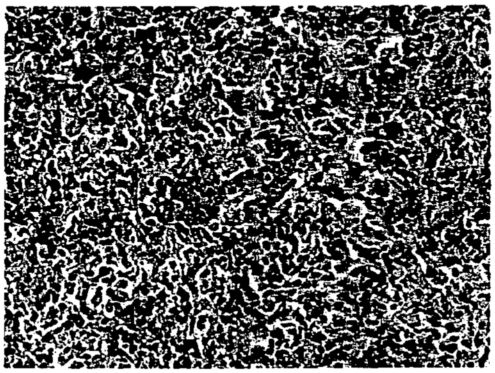
Figure 10E:
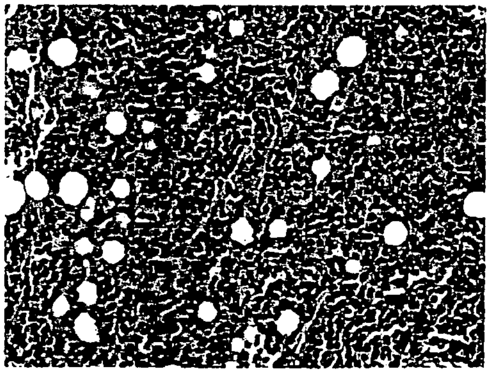
Figure 10F:
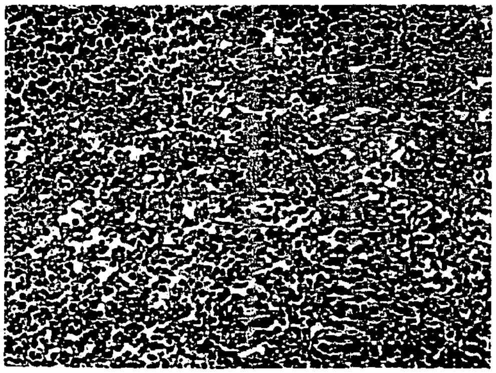

In SCID Beige mice, neoplasms were inoculated either with EBV-infected ATCC CCL-86 (left side) or with EBV-uninfected ATCC CRL-1648 (right side) Burkitt Lymphoma cells respectively at forelimb armpits of the same mouse and grew up to 1×1×1 mm in 7 days. The 20-d treatment was started eight days after the tumor cell inoculation. Pheromonicin was injected intraperitoneally each day (0.28 μM/gram bodyweight/day). At the end of treatment, the right neoplasms of treated mice (n=10) grew up to 8×6×2 mm or larger as well as both neoplasms of controls (n=10, intraperitoneal spared stock solution 0.5 ml/day) (FIGS. 10A and B). Whereas the left neoplasm sizes of treated mice were 3×2×2 mm or smaller (FIG. 10B). Neoplasms were isolated carefully and weighted for quantitative analysis. Microscopic examination demonstrated that mass proliferation existed in all CRL-1648 neoplasms of treated mice, CRL-1648 and CCL-86 neoplasms of controls (FIG. 10C-E). Whereas either coagulative necrosis spread to the entire cell population or only necrotic entities remained in the CCL-86 neoplasms of treated mice (FIG. 10F).

Figure 11A:
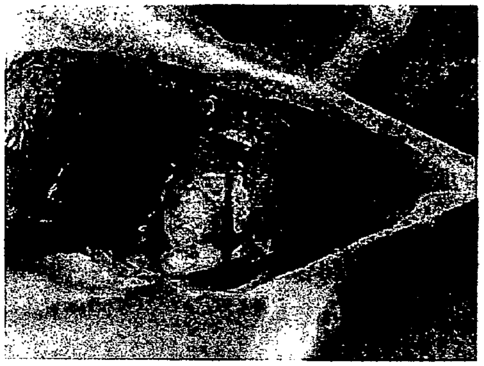
FIG. 11A is a CCD image of cells treated with stock solution of pheromonicin as a control.
Figure 11B:
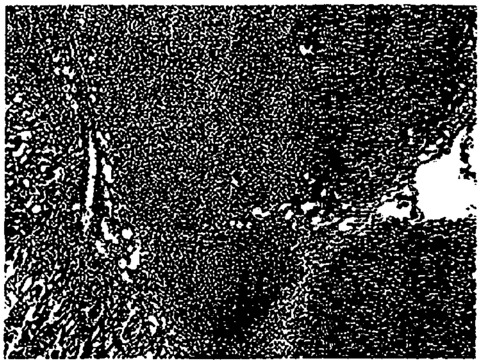
Figure 11C:
Figure 11D:
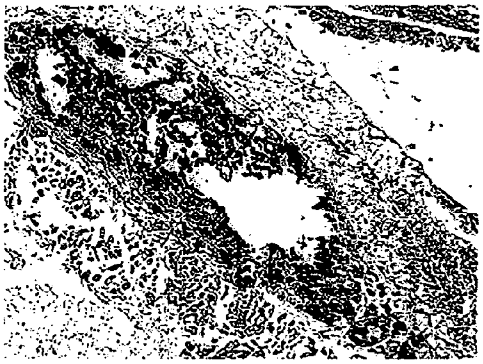
Figure 11E:
Figure 11F:
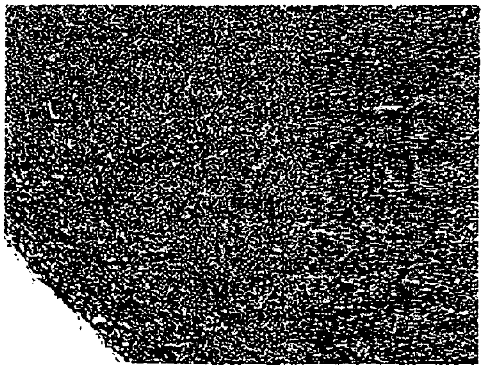

In BALB/C nude mice, only EBV-infected ATCC CCL-86 inoculated at right forelimb armpit area. The 20-d intraperitoneal pheromonicin treatment started at the $8^{th}$ day of inoculation while the neoplasms grew up to 1×1×1 mm in all mice. At the end of the 20-d experimental period, neoplasm of control mice (n=10, intraperitoneal spared stock solution 0.5 ml/day) grew up to 8×6×3 mm or larger (FIG. 11A). Whereas the neoplasms of treated mice (n=10, intraperitoneal pheromonicin 0.27 nM/gram bodyweight/day) either disappeared or shrank to smaller than 1×1×1 mm sizes with bodyweight gaining. Autopsy found that either neoplasm were smaller than 1×1×1 mm in 7 of them or no visible neoplasm detected in the rest three (FIG. 11C). Microscopic examination demonstrated that only necrotic entities remained in either visible or microscopic neoplasm with pheromonicin treatment (FIG. 11D). Three in vivo assays were done for control and pheromonicin treatment respectively.

Figure 11G:
Figure 11H:
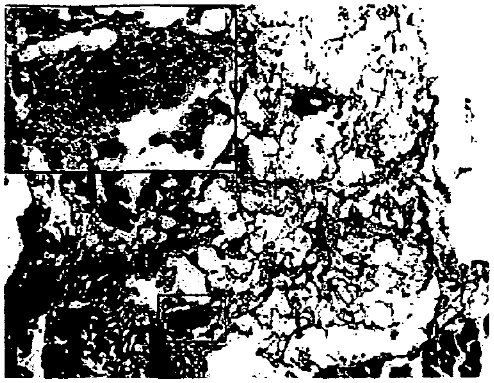
Figure 11I:
Figure 11J:
Figure 11K:
Figure 11L:
FIG. 11L depicts 100× microscope image of the xenograft. Inset: enlarged view of rectangle area where nasopharyngeal cells were undergoing coagulative necrosis (arrows).

To determine whether that elimination activity of pheromonicin was universal to other EBV-infected tumors, AIDS related body cavity based lymphoma (ATCC CRL-2230 strain, EBV+)(AIDSL) and nasopharyngeal cancer (TNE-1 strain, EBV+, Institute of Cancer Research, Hunan University of Medical Sciences, Changsha, Hunan, China)(NC) cells were inoculated into BALB/C nude mice respectively and mice were treated as to what performed in the BL experiment. FIG. 11G-H shows that pheromonicin presented identical elimination effects in the AIDSL neoplasm. The NC neoplasm, however, was not eliminated so keen as to what occurred in the BL and AIDSL cases. At the end of 20-d treatment, encapsulated NC cells were undergoing coagulative necrosis in the shrunk NC neoplasm (Inset of FIG. 11L).

Taken together, there were 30 treated cases and 30 control cases in each BL, AIDSL and NC experiments. Total weight of all visible neoplasms in control or treated experiments (no visible neoplasm were counted as zero) was added up for quantitative analysis. There were statistically significance differences in total weight of neoplasms between control and treated BL neoplasm (p<0.0.001), AIDSL neoplasm (p<0.0.001) and NC neoplasm (p<0.0.001).

Example 3

In Vivo Penetration Effects into Solid Tumor Model in Immunodeficiency Mice

In vivo distribution of circulating pheromonicin molecules were observed with fluorescent-labeling imagine system in the animals with an inoculated xenograft. One hour after intraperitoneal injection, the FITC-labeled pheromonicin molecules started to accumulate inside the implanted solid tumor of EBV-induced cells. The accumulation lasted approximately 6 hours. At least half of the systemic distributed pheromonicin had been cleared by approximately 4 hours after injection through urination (FIGS. A-D). Conversely, there was no accumulation in the implanted solid tumor of EBV-uninfected cells. In addition, there was no accumulation of the FITC-labeled HB-168 monoclonal IgG against EBV gp350/220 envelope antigen, the template of mimetic targeting segment of Ph-EBV, in either EBV-induced tumor or EBV-uninfected tumor. There was some accumulation encircling the boundaries of the EBV-induced tumor (FIG. E-F). PMC-SA, a control pheromonicin against *Staphylococcus aureus* fused to a staphylococcal pheromone to colicin Ia, did not present any specific accumulation in both tumors but presented identical systemic distribution and clearance of pheromonicin-EBV molecules (FIG. G). These results indicate that at least in tested mice, pheromonicin was cleared rapidly and had much better penetration and accumulation abilities than that of intact IgG molecules against targeted solid tumors.

Example 4

Assessment of Toxicity of Pheromonicin to Mammalian Cells

There was no microscopic evidence of necrosis or inflammation in the livers, intestines, kidneys or spleens of the regular mice received 30-day intraperitoneal pheromonicin treatment (700 μg/mouse/day)(n=10)(FIG. 13A-D). These data suggest that pheromonicin may be tolerated by mammalian systems without evident toxicity.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a subject mammal having a cell proliferative disorder, the method comprising:

administering to said subject mammal an effective amount of a fusion polypeptide comprising a cancer cell targeting agent that targets mammalian cancer calls covalently attached to a channel-forming moiety, thereby treating said subject, the channel-forming moiety being a colicin or channel-forming domain thereof.

2. The method of claim 1, wherein said targeting agent is selected from an antibody, an antibody fragment, and a reconstructed antibody mimetic.

3. The method of claim 2, wherein said targeting agent is specific for a polypeptide that is differentially expressed in cancer cells.

4. The method of claim 1, wherein said channel-forming moiety colicin is selected from the group consisting of colicin E1, Ia, Ib, A, K or N.

5. The method of claim 1, wherein said colicin is colicin Ia or channel-forming fragment thereof.

6. The method of claim 5, wherein said channel-forming fragment of colicin Ia comprises 451-626 amino acid residues of colicin Ia in SEQ ID NO: 1.

7. The method of claim 1, wherein said cell proliferative disorder is cancer.

8. The method of claim 7, wherein said cancer is a viral associated cancer.

9. The method of claim 7, wherein said cancer is selected from the group consisting of a cancer formed in the larynx, the prostate, the stomach, the skin, the oral cavity, the pharynx, the esophagus, the liver, the lung, the head, the neck, the bronchus, the pancreas, the small intestine, the colon, the rectum, the breast, the bladder, the uterus, the brain, the lymph system, the blood, the ovaries, the kidneys, and soft tissue.

10. A method of treating a subject mammal having a cell proliferative disorder, the method comprising:

administering to said subject mammal an effective amount of a fusion polypeptide comprising a cancer cell targeting reconstructed antibody mimetic derived from engineered antibody against Epstein-Barr virus gp350/220 envelope glycoprotein complex that targets mammalian cancer cells and a channel-forming domain of colicin covalently linked to the cancer cell targeting moiety, thereby treating said subject.

11. The method of claim 10, wherein said reconstructed antibody mimetic comprises two CDRs of the antibody and a polypeptide linker, wherein the two CDRs are covalently linked by the polypeptide linker, wherein said antibody specifically binds Epstein-Barr virus gp350/220 envelope glycoprotein complex.

12. The method of claim 11, wherein one of the CDR is CDR1 of a heavy chain variable domain and the other CDR is CDR3 of a light chain variable domain.

13. The method of claim 12, the amino acid sequence of the reconstructed antibody mimetic is SEQ ID NO: 5.

14. The method of claim 11, wherein said polypeptide consisting essentially of the amino acid sequence of SEQ ID NO: 7.

15. The method of claim 1, further comprising obtaining a nucleic acid molecule encoding the fusion polypeptide.

16. The method of claim 15, further comprising transfecting a host cell with the nucleic acid molecule so that the host cell produces the fusion polypeptide.

17. The method of claim 16, wherein said nucleic acid molecule has the nucleic acid sequence of SEQ ID NO: 8.

18. The method of claim 10, further comprising obtaining a nucleic acid molecule encoding the fusion polypeptide.

19. The method of claim 18, further comprising transfecting a host cell with the nucleic acid molecule so that the host cell produces the fusion polypeptide.

* * * * *

UNITED STATES PATENT AND TRADEMARK OFFICE

CERTIFICATE OF CORRECTION

PATENT NO. : 8,722,050 B2
APPLICATION NO. : 13/708767
DATED : May 13, 2014
INVENTOR(S) : Qiu

It is certified that error appears in the above-identified patent and that said Letters Patent is hereby corrected as shown below:

On the Title Page, Item (56), under "OTHER PUBLICATIONS", in Column 2, Line 45, delete "Escherichia coil" and insert -- Escherichia coli --, therefor.

On the Title Page, Item (56), under "OTHER PUBLICATIONS", in Column 2, Line 48, delete "Escherichia coil," and insert -- Escherichia coli, --, therefor.

In the Specification

In Column 3, Line 33, delete "FIB-168" and insert -- HB-168 --, therefor.

In Column 3, Line 40, delete "FIG. 3A-B" and insert -- FIGS. 3A-B --, therefor.

In Column 3, Line 48, delete "FIG. 4A-B" and insert -- FIGS. 4A-B --, therefor.

Figure 5A:
FIG. 5A-B depict images of human EBV-uninfected Burkitt's malignant lymphoma cells after 72 hours of treatment with Ph-EBV.
Figure 5B:

In Column 3, Line 56, delete "FIG. 5A-B" and insert -- FIGS. 5A-B --, therefor.

Figure 6A:
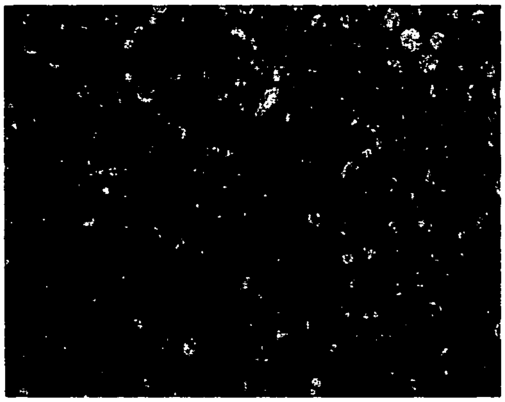
FIG. 6A-B depict images of human EBV-infected AIDS related body cavity based lymphoma cells after 72 hours of treatment with Ph-EBV.
Figure 6B:
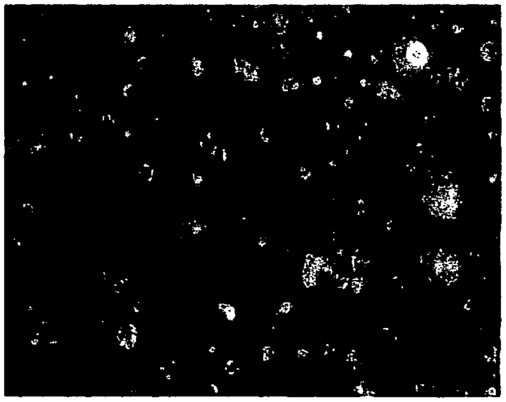

In Column 3, Line 63, delete "FIG. 6A-B" and insert -- FIGS. 6A-B --, therefor.

Figure 7A:
FIG. 7A-B depict images of SMMC-7721 human hepatocellular cancer cells after 72 hours of treatment with Ph-EBV.
Figure 7B:

In Column 4, Line 4, delete "FIG. 7A-B" and insert -- FIGS. 7A-B --, therefor.

Figure 8A:
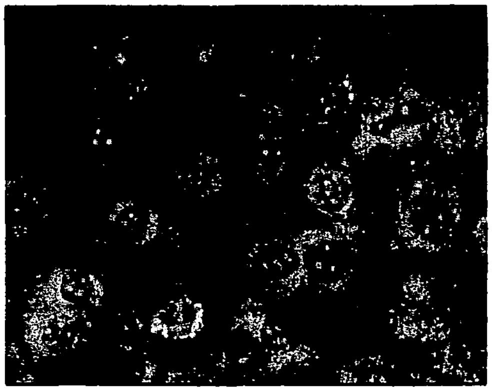
FIG. 8A-B depict images of ATCC 3T3 mouse fibroblast cells after 72 hours of treatment with Ph-EBV.
Figure 8B:
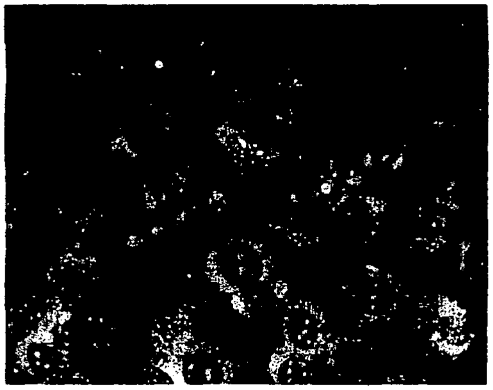

In Column 4, Line 11, delete "FIG. 8A-B" and insert -- FIGS. 8A-B --, therefor.

Figure 9A:
FIG. 9A-B depict images of ECV-304 human umbilical cord vein endothelium cells after 72 hours of treatment with Ph-EBV.
Figure 9B:

In Column 4, Line 18, delete "FIG. 9A-B" and insert -- FIGS. 9A-B --, therefor.

In Column 4, Line 25, delete "FIG. 10A-F shows" and insert -- FIGS. 10A-F show --, therefor.

In Column 4, Line 39, delete "FIG. 11A-K shows" and insert -- FIGS. 11A-K show --, therefor.

Signed and Sealed this
Second Day of September, 2014

Michelle K. Lee
*Deputy Director of the United States Patent and Trademark Office*

In Column 5, Line 13, delete “FIG. 13A-D shows” and insert -- FIGS. 13A-D show --, therefor.

In Column 7, Line 7, delete “pf” and insert -- of --, therefor.

In Column 8, Line 21, delete “squirrels.” and insert -- squirrels, --, therefor.

In Column 17, Line 15, delete “peptide (SEQ ED NO:11)” and insert -- peptide (SEQ ID NO:11) --, therefor.

In Column 19, Line 7, delete “urination (FIGS. A-D).” and insert -- urination (FIGS. 12A-D). --, therefor.

Figure 12A:
FIGS. 12A-G show the targeting distribution of circulating FITC-labeled Ph-EBV, Ph-SA or HB-168 IgG molecules in immunodeficiency mice with EBV-infected and EBV-uninfected Burkitt Lymphoma xenografts. Xenografts of a BALB/C nude mouse were inoculated either with EBV-infected (right side) or with EBV-uninfected (left side) Burkitt Lymphoma cells at respective forelimb armpits of the same mouse.
Figure 12B:
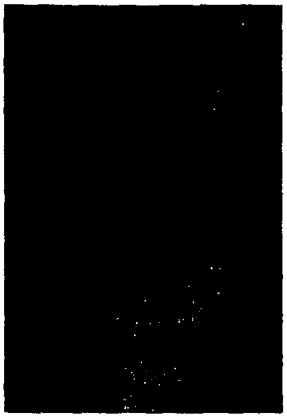
Figure 12C:
Figure 12D:
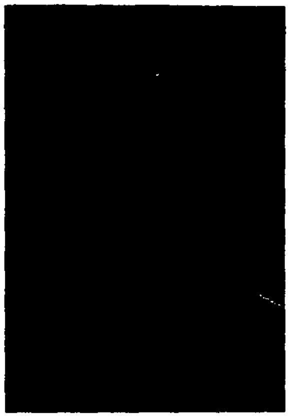
Figure 12E:
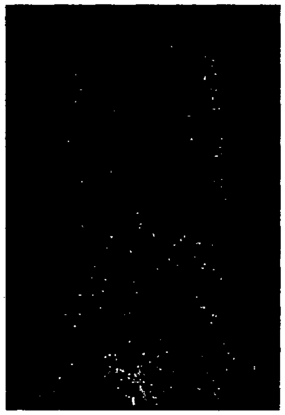
Figure 12F:
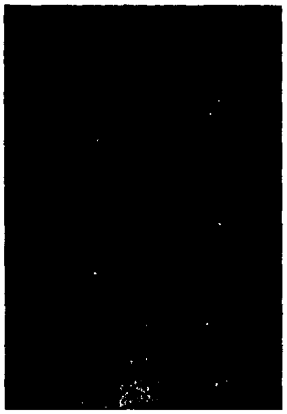

In Column 19, Line 15, delete “(FIG. E-F).” and insert -- (FIGS. 12E-F). --, therefor.

Figure 12G:
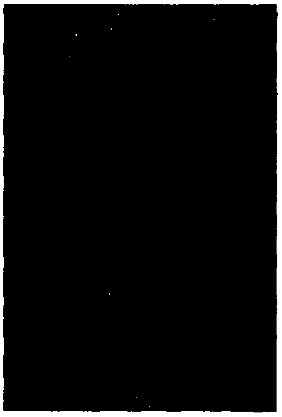
Figures 13A, 13B, 13C, 13D:
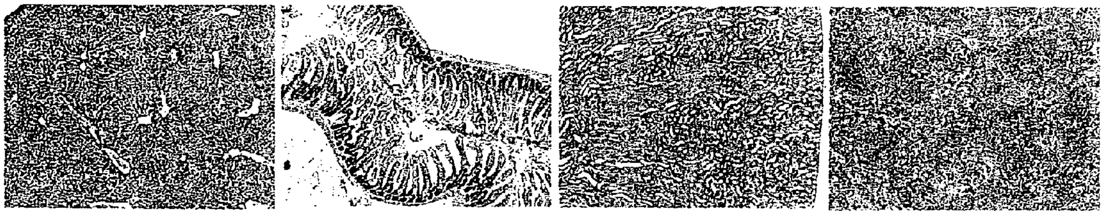
FIG. 13A-D shows the presence or absence damage in visceral organs of regular mouse after 30-day intraperitoneal Ph-EBV treatment (700 μg/mouse/day).

In Column 19, Line 19, delete “(FIG. G).” and insert -- (FIG. 12G). --, therefor.

In the Claims

In Column 37, Line 45, in Claim 1, delete “calls” and insert -- cells --, therefor.